US008465960B2

(12) United States Patent
Kawaoka et al.

(10) Patent No.: US 8,465,960 B2
(45) Date of Patent: Jun. 18, 2013

(54) INFLUENZA B VIRUSES WITH REDUCED SENSITIVITY TO NEURAMINIDASE INHIBITORS

(75) Inventors: Yoshihiro Kawaoka, Middleton, WI (US); Shuji Hatakeyama, Tokyo (JP)

(73) Assignee: Wisconsin Alumni Research Foundation, Madison, WI (US)

(*) Notice: Subject to any disclaimer, the term of this patent is extended or adjusted under 35 U.S.C. 154(b) by 238 days.

(21) Appl. No.: 12/058,389

(22) Filed: Mar. 28, 2008

(65) Prior Publication Data

US 2008/0293040 A1    Nov. 27, 2008

Related U.S. Application Data

(60) Provisional application No. 60/920,486, filed on Mar. 28, 2007.

(51) Int. Cl.
*C12N 7/00* (2006.01)

(52) U.S. Cl.
USPC ............. 435/235.1; 424/204.1; 424/205.1; 424/206.1; 424/209.1

(58) Field of Classification Search
None
See application file for complete search history.

(56) References Cited

FOREIGN PATENT DOCUMENTS

| WO | WO-2009/008921 A2 | 1/2009 |
|---|---|---|
| WO | WO-2009008921 A3 | 1/2009 |
| WO | WO-2009008921 A9 | 1/2009 |

OTHER PUBLICATIONS

Jackson et al., Characterization of recombinant influenza B viruses with key neuraminidase inhibitor resistance mutations, 2005, Journal of Antimicrobial Chemotherapy, vol. 55, pp. 162-169.*
Genbank Accession # AAA43733, Neuraminidase Protein of Influenza B/Beijing/1/87 virus, 1993.*
McCullers et al., Multiple Genotypes of Influenza B Virus Circulated between 1979 and 2003, 2004, Journal of Virology, vol. 78, No. 23, pp. 12817-12828.*
Genbank Accession # AAU94753, Neuraminidase Protein of Influenza B/Aichi/5/88 virus, 2004.*
Hurt et al., Identification of a human influenza type B strain with reduced sensitivity to neuraminidase inhibitor drugs, 2004, Virus Research, vol. 103, pp. 205-211.*
Genbank Accession # ABA02233, Neuraminidase Protein of Influenza B/Perth/211/2001 virus, 2006.*
McSharry et al., Phenotypic Drug Susceptibility Assay for Influenza Virus Neuraminidase Inhibitors, 2004, Cinical and Diagnostic Laboratory Immunology, vol. 11, No. 2, pp. 21-28.*
Genbank Accession #, neuraminidase influenza virus B/memphis/20/96, 1999.*
Gubareva, Molecular mechanisms of influenza virus resistance to neuraminidase inhibitors, 2004, Virus Research, vol. 103, pp. 199-203.*
Bowie et al., Deciphering the Message in Protein Sequences: Tolerance to Amino Acid Substitutions, 1990, Science, vol. 247, No. 4948, pp. 1306-1310.*
"International Application Serial No. PCT/US2008/004125, International Search Report mailed Feb. 20, 2009", 6 pgs.
"International Application Serial No. PCT/US2008/004125, Written Opinion mailed Feb. 20, 2009", 8 pgs.
"Neuraminidase [Influenza A virus (A/Aichi/2/1968 (H3N2))]", *GenBank: BAD16642.1. NCBI,* [online]. Retrieved from the Internet: <URL: http://www.ncbi.nlm.nih.gov/protein/46401580>, (2008), 3 pgs.
"Neuraminidase [Influenza B virus]", *GenBank: CAB71147.1, NCBI,* [online]. Retrieved from the Internet: <URL: http://www.ncbi.nlm.nih.gov/protein/6851026>, (2005), 3 pgs.
Burmeister, W. P., et al., "The 2.2 Å resolution crystal structure of influenza B neuraminidase and its complex with sialic acid", *The EMBO Journal*, 11(1), (1992), 49-56.
Chang, M. W., et al., "Analysis of HIV Wild-Type and Mutant Structures via in Silico Docking against Diverse Ligand Libraries", *J. Chem. Inf. Model.*, 47(3), (2007), 1258-1262.
Coleman, P. M., et al., "Sequence and Structure Alignment of Paramyxovirus Hemagglutinin-Neuraminidase with Influenza Virus Neuraminidase", *Journal of Virology*, 67(6), (1993), 2972-2980.
Hatakeyama, S., et al., "Emergence of Influenza B Viruses With Reduced Sensitivity to Neuraminidase Inhibitors", *Journal of the American Medical Association*, 297(13), (2007), 1435-1442.
Hatakeyama, S., et al., "The molecular basis of resistance to anti-influenza drugs", (w/ English Abstract), *Japanese Journal of Clinical Medicine—Nippon Rinsho*, 64(10) (2006), 1845-1852.
Monto, A. S, et al., "Detection of influenza viruses resistant to neuraminidase inhibitors in global surveillance during the first 3 years of their use", *Antimicrobal Agents and Chemotherapy*, 50(7), (2006), 2395-2402.
Puzelli, S., et al., "Changes in the Hemagglutinins and Neuraminidase of Human Influenza B Viruses Isolated in Italy During the 2001-02, 2002-03, and 2003-04 Seasons", *Journal of Medical Virology*, 74(4), (2004), 629-640.
Yagi, Y., et al., "In silico panning for a non-competitive peptide inhibitor", *BMC Bioinformatics*, 8(11), (2007), 11 pgs.

* cited by examiner

*Primary Examiner* — Benjamin P Blumel
(74) *Attorney, Agent, or Firm* — Schwegman Lundberg & Woessner, P.A.

(57) ABSTRACT

An isolated influenza B virus which has reduced sensitivity to one or more neuraminidase (NA) inhibitors, wherein the reduced sensitivity to one or more NA inhibitors is associated with a residue in NA other than Ile at position 222, a residue in NA other than Ser at a position 250, or a residue in NA other than Gly at position 402, as well as methods to detect such a virus or determine agents that inhibit the infection or replication of such as virus, are provided.

17 Claims, 9 Drawing Sheets

```
              10         20         30         40         50         60         70         80
N2  MNPNQKIITIGSVSLTIATVCFLMQI-AILVTTVTLH---FKQHECDSPASNQVMPCEPIIERNITEIVYLNNTTIEKEI----CPK------VVEY
N1  MNPNQKIITIGSICLVVGLISLILQI-G----NIISI---WISHSIQTGSQNHTGICN------QNII-TYKNST------WVKDTTSV------I
N5  MNPNQKIITIGSASLGLVIFNILLHV-A----SITL------GIISVTKDNKVHICN------TTEV-YNETVRVETVV--IPVNNTIYLNHEPE--F
N7  MNPNQKLFASSGIAIVLGIINLLIGI-SNMSLNISLY---SKG-ESH---KNNNLTCTNINQNDTTMVNTYINNATII-D------KSTKIENPG---Y
N8  MNPNQKIIAIGSASLGLILNVILHV-V----SIIV------TVLVLNNNGTGLNCN------GTIIREYNETVRVERITQWYNTNTIEYIERPSNEY
N9  MNPNQKILCTSATALVIGTIAVLIGI-TNLGLNIGLH---LKP-SCN---CSHSQP--EATNASQTIINNYYNDTNIT-QI----SNTNIQVEERAIRDF
B   MLPS----TIQTLTLFLTSGGVLLSLYVSASLSYLLYSDILLKFSPKITAPTMTLDCTNASNVQAVNRSATKEMTFLLPEPEWT-------Y
     *  *

90        100        110        120        130        140        150        160        170        180
N2  RNWSKPQCQITGFAPFSKDNSIRLSA---GGDIWVTREPYVSCDPVKCYQFALGQGTTLDNKHSNDTVHDRIPHRTLLMNELGVPFHLGTRQV-CIAWSS
N1  LTGNSSLCPIRGWAIYSKDNSIRIGS---KGDVFVIREPFISCCSHLECRTFFLTQGALLNDRHSMGTVKDRSPYRALMSCPVGEAPSPYNSRFESVAWSA
N5  LNNTEPLCDVSGFAIVSKDNGIRIGS---RGHIFVIREPFVSCGPSECRTFFLTQGALLNDKHSNNTVKDRSPYRALMSVPLGSSPNAYQAKFESVGWSA
N7  LLLNKSLCNVEGWVVIAKDNAIRFGE---SEQIIVTREPYVSCDPLSCKMYALHQGTTIRNKHSNSTTHDRTAFRGLISTPLGSPPTVSNSEFICVGWSS
N8  MNNTEPLCEAQGFAPFSKDNGIRIGS---RGHVFVIREPFVSCSPLECRTFFLTQGSLLNDKHSMGTVKDRSPYRTLMSVKVGQSPNVYQARFESVAWSA
N9  NNLTKGLCTINSWHIYGKDNAVRIGE---DSDVLVTREPYVSCDPDECRFYALSQGTTIRGKHSNGTIHDRSQYRALISWPLSSPPTVYNSRVECIGWSS
B   PRLS----CQGSTFQKALLISPHRFGEARGNSAPLIIREPFIACGPKECKHFALTHYAAQPGGYYNGTREDRNKLRHLISVKLGKIPTVENSIFHMAAWSG
                *          *      *** *        *  *  *     *     *   * **    ** ***    **

FIG. 6A
```

```
              190       200       210       220       230       240       250       260       270       280
N2  SSCHDGKAWLHVCITGDDKNATASFIYDGRLVDSIGSWSQNILRTQESECVCINGTCTVMTDGSASGRADTRILFIEEGKIVHISPLAGSAQHVEECSC
N1  SACHDGMGWLTIGISGPDNGAVAVLKYNGIITETIKSWRKKILRTQESECACVNGSCFTIMTDGPSDGLASYKIFKIEKGKVTKSIELNAPNSHYEECSC
N5  TACHDGKKWMAIGVSGADDDAYAVIHYGGVPTDVIRSWRKQILRTQESSCVCIKGECYWMTDGPANNQASYKIFKSQKGMVVDEKEISFQGGHIEECSC
N7  TSCHDGVNRMTICVQGDNENATATVYYNKRLTTTIKTWAKNILRTQESECVCHNSTCVVVMTDGPANNQAFTKVIYFHKGMIIKEESLKGSAKHIEECSC
N8  TACHDGKKWMTVGVTGPDNQAVAVVNYGGVPVDIINSWGRDILRTQESSCTCIKGDCYWMTDGPANRQAKYRIFKAKDGRIIGQTDISFNGGHIEECSC
N9  TSCHDGKTRMSICISGPNNNASAVIWYNRRPVTEINTWARNILRTQESECVCHNGVCPVVFTDGSATGPAETRIYYFKEGKILKWEPLAGTAKHIEECSC
B   SACHDGREWTYIGVDGPDSNALIKIKYGEAYTDTYHSYANNILRTQESACNCIGDDCYLMITDGSASGISKCRFLKIREGRIIKEIFPTGRVEHTEECTC
    ****                *                 *           *******  *  ***  *            ***              * *** *

290       300       310       320       330       340       350       360       370
N2  -YPRYPGVRCICRDNWKGSNRPVVDINMEDYSIDSSYVCSGLVGDTPRNDDRSSNSNCRNP-NNERGTQ-GVKGWAFDNGN------DLWMGRTISKDLRS
N1  -YPDTGKVMCVCRDNWHGSNRPWVSFD-QNLDYQIGYICSGVFGDNPRPKDG--TGSCGPVYVDGAN---GVKGFSYRYGN------GVWIGRTKSHSSRH
N5  -YPNMGKVECVCRDNWNGMNRPILIFD-EKLEYEVGYLCAGIPTDTPRVQDSSFTGSCTNAVGRSGTNNYGVKGFGFRQGN------SVWAGRTISVSSRS
N7  -YGHNQRVTCVCRDNWQGANRPIIEIDMNKLEHTSRYICTGVLTDTSRPKDKTI-GECFNPITGSPGAP-GIKGFGFLNED------NTWLGRTISPRLRS
N8  -YPNEGKVECVCRDNWTGTNRPILVIS-PDLSYTVGYLCAGIPTDTPRGEDSQFTGSCTSPLGNKG----YGVKGFGFRQGN------DVWAGRTISRTSRS
N9  -YGERAEITCTCRDNWQGSNRPVIRIDPVAMTHTSQYICSPVLTDNPRPNDPTV-GKCNDPYPGN-NNN-GVKGFSYLDGV------NTWLGRTISIASRS
B   GFASNKTIECACRDNNYTAKRPFVKLNVETDTAEIRLMCTETYLDTPRPDDGSITGPCESNGDKGRG---GIKG-GFVHQRMASKIGRWYSRTMSKTERM
      *        *      **  *                          *            *           * ***           *  ** * *
```

FIG. 6B

```
         380       390       400       410       420       430       440       450       460
N2  GYETFKVIGG---WSTPNSKSQINRQVIVDSDNRSGYSGIFS----V-EGKSCINTCFYVELIRGRKQETR-VWWTSNSIVVFCGTSGTYGTGSWPDGANIN
N1  GFEMIWDPNG---WTETD-SKFSVRQDVVAMTDWSGYSGSFVQHPELTGLDCIRPCFWVELIRGRPKEKT-I-WTSASSISFCGVNSDTVDWSWPDGAELP
N5  GFEVLLIEDG---WIRPS-KTISKKVEVLNNKNWSGYSGAFTIPTAMTSKNCIVPCFWLEMIRGKPEERTSI-WTSSSSTVFCGVSSEVPGWSWDDGAILP
N7  GFEMLKIPNA---GTDPESKIK-ERQEIVSNDNWSGYSGSFIDYWN-DNSECYNPCFYVELIRGRPEEAKYVEWTSNSLIALCGSPISVGSGSFPDGAQIK
N8  GFEIIKIRNG---WTQNS-KDQIRKQVIIDNLNWSGYSGSFTLPVELTKKGCLVPCFWVEMIRGKPED-TTI-WTSSSSIVMCGVDHKIASWSHDGAILP
N9  GYEMLKVPNA---LTDDKSKPT-QGQTIVLNTDWSGYSGSEMDYWA-E-GECYRACFYVELIRGRPKEDK-VWWTSNSIVSMCSSTEFLGQWDWPDGAKIE
B   GMELYVKYDGDPWTDSDALDPSGVMVSIKEPGW--YSFGF----EIKDKKCDVPCIGIEMVHDGGKKT----WHSAATAIYCLMGS--GQLLWDTVTGVD
         *  *                                    **  *        *           *         **   **          *

470
N2  FM--PI
N1  FTIDK-
N5  FDIDKM
N7  YF---S
N8  FDIDKI
N9  YF---L
B   M---AL
```

*FIG. 6C*

Primers used for amplification of the neuraminidase and hemagglutinin genes of influenza B viruses

| Assay | Primer | Direction | Sequence (5' → 3') | Position |
|---|---|---|---|---|
| RT | Bm-NAb-1* | Forward | *TATTCGTCTCAGGGAGCAGAAGCAGAGCA* | |
| PCR | Bm-NAb-29Fo* | Forward | *TATTCGTCTCAGGGAGCAGAAGCAGAGCATCTTCTCAAAACTG* | |
| | Bm-NAb-28Re* | Reverse | *ATATCGTCTCGTATTAGTAGTAACAAGAGCATTTTTCAGAAAC* | |
| | Bm-HAb-30Fo* | Forward | *TATTCGTCTCAGGGAGCAGAAGCAGAGCATTTTCTAATATCC* | |
| | Bm-HAb-33Re* | Reverse | *ATATCGTCTCGTATTAGTAGTAACAAGAGCATTTTTCAATAACGTTTC* | |
| Sequence | B-NA-1R | Reverse | TGCCTCAGCTTGTTCTGTC | 498-517 |
| | B-NA-2F | Forward | GAAAGCACTCCTAATTAGCCC | 333-353 |
| | B-NA-3F | Forward | GACACAAGAAAGTGCCTGCA | 722-741 |
| | B-NA-4F | Forward | GAATGGCATCCAAGATTGGAAG | 1120-1141 |
| | B-HA-1R | Reverse | TGTAGGGTCCTCCTGGTGC | 466-484 |
| | B-HA-2F | Forward | GCTTTCCTATAATGCACGAC | 359-378 |
| | B-HA-3F | Forward | GAATTGTTGTTGATTACATG | 809-828 |
| | B-HA-4F | Forward | GATGAGAAAGTGGATGATCT | 1357-1376 |

Abbreviations: RT, reverse transcription; PCR, polymerase chain reaction

- The 5'-end has recognition sequences for *Bsm*B I restriction endonuclease (indicated in italics).

*FIG. 7*

INFLUENZA B VIRUSES WITH REDUCED SENSITIVITY TO NEURAMINIDASE INHIBITORS

CROSS-REFERENCE TO RELATED APPLICATIONS

This application claims the benefit of the filing date of U.S. application Ser. No. 60/920,486, filed on Mar. 28, 2007, the disclosure of which is incorporated by reference herein.

STATEMENT OF GOVERNMENT RIGHTS

The invention was made, at least in part, with a grant from the Government of the United States of America (grant AI069274 from the National Institutes of Health). The Government has certain rights in the invention.

BACKGROUND

Clinical use of any antiviral drug can lead to the development of drug-resistant viruses (Pillay et al., 1998; De Clercq, 2004). Two neuraminidase (NA) inhibitors, oseltamivir and zanamivir, have proven effective against influenza and are used extensively to combat this infection, especially in Japan (Ward et al., 2005; Roche, 2005). There is documentation of the emergence of oseltamivir-resistant type A viruses, including H5N1 subtypes (Ward et al., 2005; Kiso et al., 2004; Le et al., 2005; de Jong et al., 2005), but similar information on influenza B viruses with reduced sensitivity to NA inhibitors is limited. Although influenza B viruses usually cause smaller epidemics than type A viruses, they are nonetheless associated with annual outbreaks of illness and excess mortality rates worldwide (Treanor et al., 2005).

Of the two type B viruses with reduced sensitivity that have been reported, one carried an Arg152Lys mutation (amino acid numbering system adapted for an N2 NA, see Colman et al., 1993; N2 numbering is used herein) in its NA and was isolated from an immunocompromised child treated with zanamivir (Gubareva et al., 1998). The other had an Asp198Asn NA mutation and was isolated from an immunocompromised child treated with oseltamivir (Gubareva, 2004). The known NA substitutions identified in drug-resistant viruses from humans tend to be type- or subtype-specific: Glu119Val, Arg292Lys and Asn294Ser in the NA of the N2 subtype, His274Tyr in the N1 subtype (including not only H1N1 viruses but also H5N1 viruses) (Le et al., 2005; de Jong et al., 2005), and Arg152Lys and Asp198Asn in the NA of type B virus (Gubareva et al., 1998; Gubareva, 2004). All of these substitutions have been identified at catalytic or framework residues in the sialidase active site of the NA protein (Colman et al., 1993), which are relatively conserved in all type A and type B NA molecules and are the targets of NA inhibitors.

The results of cell culture experiments in which multiple passages were required for the generation of NA inhibitor-resistant viruses (McKimm-Breschkin, 2000) suggested that resistance to these agents arises infrequently. It is thus reasonable that a low frequency of oseltamivir resistance, 5.5% for children aged 1-12 years infected with type A viruses and none in children infected with type B virus, was observed in a clinical trial (Whitley et al., 2001). However, more recent studies demonstrated a higher-than-expected rate of drug-resistant influenza A virus generation in oseltamivir-treated children: 18% of children with H3N2 virus infection and 16% of those with H1N1 virus infection (Ward et al., 2005) harbored resistant variants with NA mutations after drug treatment.

Very little is known about the frequency of generation and transmissibility of influenza B viruses with reduced sensitivity to neuraminidase (NA) inhibitors. Further, transmission of resistant variants, whether type A or B virus, has yet to be shown.

SUMMARY OF THE INVENTION

The rapid identification of the susceptibility status of influenza B viruses allows for the selection of an efficacious course of treatment. The invention provides methods to identify influenza B virus isolates that are resistant to one or more NA inhibitors, or alternatively, susceptible to one or more NA inhibitors. "Resistance" or "reduced sensitivity" of an influenza B virus isolate to an NA inhibitor as used herein includes an $IC_{50}$ value that is at least 2-fold, e.g., about 3- to about 6-fold or more, greater than a corresponding NA inhibitor sensitive influenza B virus isolate. Exemplary NA inhibitors are peramivir, oseltamivir and zanamivir. In one embodiment, the corresponding NA inhibitor sensitive influenza B virus is one that has an amino acid residue at position 198, 222, 250 or 402 of NA (based on N2 numbering), or a combination thereof, that is different than the NA inhibitor resistant influenza B virus. In one embodiment, the corresponding NA inhibitor sensitive influenza B virus has an Asp at position 198, an Ile at position 222, a Ser at position 250 or a Gly at position 402 of NA. For instance, an influenza B virus isolate that is resistant to oseltamivir includes an isolate that has an $IC_{50}$ of at least 3-fold, e.g., about 3- to about 6-fold, greater than a corresponding isolate that is sensitive to oseltamivir. An influenza B virus isolate that is resistant to zanamivir has an $IC_{50}$ of at least 3-fold, e.g., about 3- to about 6-fold, e.g., about 6-fold to about 20-fold, greater than a corresponding isolate that is sensitive to zanamivir. An influenza B virus isolate that is resistant to both oseltamivir and zanamivir has an $IC_{50}$ of at least 3-fold, e.g., about 3- to about 6-fold, greater than an isolate that is sensitive to both.

As described herein, the NA inhibitor sensitivity of type B viruses isolated from 74 children before and after oseltamivir therapy, and from 348 untreated influenza patients (including 66 adults) seen at four community hospitals in Japan during the influenza season, was investigated. Thus, 422 viruses from untreated patients and 74 viruses from patients after oseltamivir therapy were analyzed. A sialidase inhibition assay was used to test the drug sensitivities of influenza B viruses. The NA and hemagglutinin (HA) genes of viruses showing reduced sensitivity to the inhibitors were sequenced to identify mutations that have the potential to confer reduced sensitivity to these drugs. In one of the 74 children (1.4%) who had received oseltamivir, a variant with reduced drug sensitivity possessing a Gly402Ser NA substitution was identified. Variants with reduced sensitivity were also identified that carried an Asp198Asn, Ile222Thr or Ser250Gly mutation in 7 (1.7%) of the 422 viruses from untreated patients. A review of the clinical and viral genetic information that was available on these cases indicated that four of the patients were likely to have been infected with such variants in a community setting, while the remaining three were probably infected through contact with siblings who were shedding the mutant viruses. While in the investigated population, influenza B viruses with reduced sensitivity to NA inhibitors did not arise as frequently as resistant influenza A viruses, they may be transmitted within communities and families, requiring continued close monitoring of such viruses.

The invention thus provides an isolated influenza B virus which has reduced sensitivity to one or more NA inhibitors, wherein the reduced sensitivity to the one or more NA inhibitors is associated with a residue in NA other than Ile at position 222, a residue in NA other than Ser at a position 250, or a residue in NA other than Gly at position 402 (the numbering for NA residues is that for N2). In one embodiment, the substitution in the NA of the isolated influenza B virus which has reduced sensitivity to one or more NA inhibitors is a nonconservative substitution. Also provided is an isolated influenza B virus which has reduced sensitivity to one or more NA inhibitors, wherein the reduced sensitivity to the one or more NA inhibitors is associated with a residue in NA other than Asp at position 198, wherein the isolated influenza B virus also has a substitution in HA, e.g., at position 426.

The invention also provides a method to detect an influenza B virus having reduced sensitivity to a NA inhibitor. The method includes detecting whether an influenza B virus isolate from a mammal, e.g., from a physiological sample, has a residue in NA other than Asp at position 198, other than Ile at position 222, other than Ser at position 250, other than Gly at position 402, or a combination thereof. In one embodiment, nucleic acid amplification and/or hybridization techniques are employed to detect the presence of a particular sequence at codons for residues 198, 222, 250, or 402 of NA, or a combination thereof, as those methods are rapid and specific. For instance, differentially labeled probes for an Asp codon and for an Asn codon at position 198 may be employed in such a method. Alternatively, labeled probes for all codons other than an Asp codon at position 198 may be employed.

Further provided is a method to screen for NA inhibitors. The method includes contacting an influenza B virus isolate that has a residue in NA other than Asp at position 198, other than Ile at position 222, other than Ser at position 250, other than Gly at position 402, or a combination thereof, with one or more test agents, and detecting whether the one or more test agents inhibit viral replication.

BRIEF DESCRIPTION OF THE FIGURES

FIG. 6. Alignment of influenza NA sequences (Colman et al., 1993). Sequence numbering corresponds to that of the N2 sequence. Asterisks indicate amino acid residues which are identical in all sequences. N2, A/Tokyo/3/67, SEQ ID NO:2; N1, A/Puerto Rico/8/34, SEQ ID NO:3; N5, A/Shearwater/Australia/72, SEQ ID NO:4; N7, A/Cor/16/74, SEQ ID NO:5; N8, A/Ken/1/81, SEQ ID NO:6; N9, A/Tern/Australia/G70C/75, SEQ ID NO:7; B, B/Victoria/3/85, SEQ ID NO:8.

FIG. 7. Sequence of primers employed to amplify influenza virus sequences. Bm-NAb-1, SEQ ID NO:9; Bm-NAb-29Fo, SEQ ID NO:10; Bm-NAb-28Re, SEQ ID NO:11; Bm-HAb-30Fo, SEQ ID NO:12; Bm-HAb-33Re, SEQ ID NO:13; B-NA-1R, SEQ ID NO:14; B-NA-2F, SEQ ID NO:15; B-NA-3F, SEQ ID NO:16; B-NA-4F, SEQ ID NO:17; B-HA-1R, SEQ ID NO:18-B-HA-2F SEQ ID NO:19-B-HA-3F SEQ ID NO:20-B-HA-4F SEQ ID NO:21.

DETAILED DESCRIPTION OF THE INVENTION

Definitions

Figure 1:
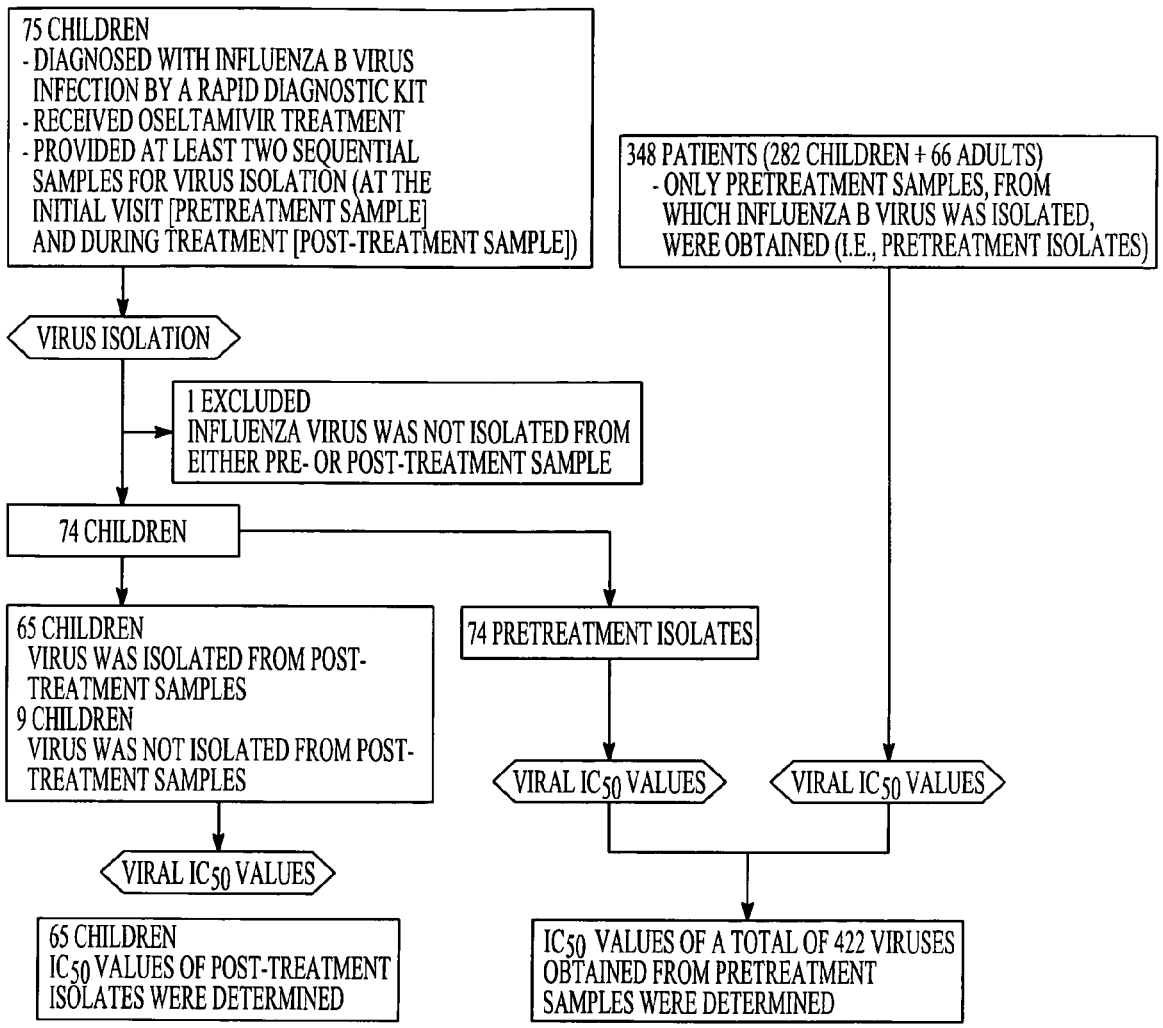
FIG. 1. Flowchart of the participants.

As used herein, the following terms have the given meanings unless expressly stated to the contrary.

As used herein, the terms "isolated and/or purified" refer to in vitro, including in silico, preparation, isolation and/or purification of a virus or NA of the invention, so that it is not associated with in vivo substances, or is substantially purified from in vitro substances. An isolated virus preparation of the invention is generally obtained by in vitro culture and propagation and is substantially free from other infectious agents. As used herein, "substantially free" means below the level of detection for a particular infectious agent using standard detection methods for that agent. A "recombinant" virus is one which has been manipulated in vitro, e.g., using recombinant DNA techniques to introduce changes to the viral genome.

A "nucleotide" is a subunit of a nucleic acid comprising a purine or pyrimidine base group, a 5-carbon sugar and a phosphate group. The 5-carbon sugar found in RNA is ribose. In DNA, the 5-carbon sugar is 2'-deoxyribose. The term also includes analogs of such subunits, such as a methoxy group (MeO) at the 2' position of ribose.

An "oligonucleotide" is a polynucleotide having two or more nucleotide subunits covalently joined together. Oligonucleotides are generally about 10 to about 100 nucleotides in length, or more preferably 10 to 50 nucleotides in length. The sugar groups of the nucleotide subunits may be ribose, deoxyribose, or modified derivatives thereof. The nucleotide subunits may be joined by linkages such as phosphodiester linkages, modified linkages or by non-nucleotide moieties that do not prevent hybridization of the oligonucleotide to its complementary target nucleotide sequence. Modified linkages include those in which a standard phosphodiester linkage is replaced with a different linkage, such as a phosphorothioate linkage, a methylphosphonate linkage, or a neutral peptide linkage. Nitrogenous base analogs also may be components of oligonucleotides in accordance with the invention. Ordinarily, oligonucleotides will be synthesized by organic chemical methods and will be single-stranded unless specified otherwise. Oligonucleotides can be labeled with a detectable label.

A "target nucleic acid" is a nucleic acid comprising a target nucleic acid sequence.

A "target nucleic acid sequence," "target nucleotide sequence" or "target sequence" is a specific deoxyribonucleotide or ribonucleotide sequence that can be hybridized by an oligonucleotide. For instance, a "target nucleic acid sequence region" of NA of influenza B virus refers to a nucleic acid sequence present in nucleic acid or a sequence complementary thereto found in the NA gene of influenza B virus, which is not present in nucleic acids of other species. Nucleic acids having nucleotide sequences complementary to a target sequence may be generated by target amplification techniques such as polymerase chain reaction (PCR).

A "primer" is a single-stranded polyoligonucleotide that combines with a complementary single-stranded target to form a double-stranded hybrid, which primer in the presence of a polymerase and appropriate reagents and conditions, results in nucleic acid synthesis.

A "probe" is a single-stranded polynucleotide that combines with a complementary single-stranded target polynucleotide to form a double-stranded hybrid. A probe may be an oligonucleotide or a nucleotide polymer, and may contain a detectable moiety which can be attached to the end(s) of the probe or can be internal to the sequence of the probe. The nucleotides which combine with the target polynucleotide need not be strictly contiguous as may be the case with a detectable moiety internal to the sequence of the probe.

A "detectable moiety" is a label molecule attached to, or synthesized as part of, a polynucleotide probe. This molecule should be uniquely detectable and will allow the probe to be detected as a result. These detectable moieties include but are not limited to radioisotopes, colorimetric, fluorometric or chemiluminescent molecules, enzymes, haptens, redox-active electron transfer moieties such as transition metal complexes, metal labels such as silver or gold particles, or even unique oligonucleotide sequences.

A "hybrid" is the complex formed between two single-stranded polynucleotide sequences by Watson-Crick base pairings or non-canonical base pairings between the complementary bases. By "nucleic acid hybrid" or "probe:target duplex" is meant a structure that is a double-stranded, hydrogen-bonded structure, preferably 10 to 100 nucleotides in length, more preferably 14 to 50 nucleotides in length. The structure is sufficiently stable to be detected by means such as chemiluminescent or fluorescent light detection, colorimetry, autoradiography, electrochemical analysis or gel electrophoresis. Such hybrids include RNA:RNA, RNA:DNA, or DNA:DNA duplex molecules.

"Hybridization" is the process by which two complementary strands of polynucleotide combine to form a stable double-stranded structure ("hybrid complementarity" is a property conferred by the base sequence of a single strand of DNA or RNA which may form a hybrid or double-stranded DNA:DNA, RNA:RNA or DNA:RNA through hydrogen bonding between Watson-Crick base pairs on the respective strands). Adenine (A) ordinarily complements thymine (T) or uracil (U), while guanine (G) ordinarily complements cytosine (C).

"Stable" means resistant to chemical or biochemical degradation, reaction, decomposition, displacement or modification.

"Stability" means the resistance of a substance to chemical or biochemical degradation, reaction, decomposition, displacement or modification.

The term "stringency" is used to describe the temperature and solvent composition existing during hybridization and the subsequent processing steps. Under high stringency conditions only highly complementary nucleic acid hybrids will form; hybrids without a sufficient degree of complementarity will not form. Accordingly, the stringency of the assay conditions determines the amount of complementarity needed between two polynucleotide strands forming a hybrid. Stringency conditions are chosen to maximize the difference in stability between the hybrid formed with the target and the non-target polynucleotide.

The term "probe specificity" or "primer specificity" refers to a characteristic of a probe or primer which describes its ability to distinguish between target and non-target sequences. Probe or primer specificity is dependent on sequence and assay conditions and may be absolute (i.e., the primer or probe can distinguish between nucleic acid from target organisms and any non-target organisms), or it may be functional (i.e., the primer or probe can distinguish between the nucleic acid from a target organism and any other organism normally present in a particular sample).

"Polynucleotide" means either RNA or DNA, along with any synthetic nucleotide analogs or other molecules that may be present in the sequence and that do not prevent hybridization of the polynucleotide with a second molecule having a complementary sequence. The term includes polymers containing analogs of naturally occurring nucleotides and particularly includes analogs having a methoxy group at the 2' position of the ribose (MeO).

A "biological sample" refers to a sample of material that is to be tested for the presence of influenza virus nucleic acid thereof. The biological sample can be obtained from an organism, e.g., it can be a physiological sample, such as one from a human patient, a laboratory mammal such as a mouse, rat, pig, monkey or other member of the primate family, by drawing a blood sample, sputum sample, spinal fluid sample, a urine sample, a rectal swab, a peri-rectal swab, a pharyngeal sample, a nasal swab, a throat swab, or a culture of such a sample, e.g., from liquid culture. Ordinarily, the biological sample will contain hybridizable polynucleotides. These polynucleotides may have been released from organisms that comprise the biological sample, or alternatively can be released from the organisms in the sample using techniques such as sonic disruption or enzymatic or chemical lysis of cells to release polynucleotides so that they are available for amplification with one or more polynucleotide primers or hybridization with a polynucleotide probe.

"$T_m$" refers to the temperature at which 50% of the probe or primer is converted from the hybridized to the unhybridized form.

One skilled in the art will understand that probes or primers that substantially correspond to a reference sequence or region can vary from that reference sequence or region and still hybridize to the same target nucleic acid sequence. Probes of the present invention substantially correspond to a nucleic acid sequence or region if the percentage of identical bases or the percentage of perfectly complementary bases between the probe and its target sequence is from 100% to 80% or from 0 base mismatches in a 10 nucleotide target sequence to 2 bases mismatched in a 10 nucleotide target sequence. In one embodiment, the percentage is from 100% to 85%. In another embodiment this percentage is from 90% to 100%; and in yet other embodiments, this percentage is from 95% to 100%. Probes or primers that substantially correspond to a reference sequence or region include probes or primers having any additions or deletions which do not prevent the probe or primer from having its claimed property, such as being able to preferentially hybridize under high stringency hybridization conditions to its target nucleic acid over non-target nucleic acids.

By "sufficiently complementary" or "substantially complementary" is meant nucleic acids having a sufficient amount of contiguous complementary nucleotides to form a hybrid that is stable for detection or to initiate nucleic acid synthesis.

By "anti-sense" is meant a nucleic acid molecule perfectly complementary to a reference (i.e., sense) nucleic acid molecule.

"RNA and DNA equivalents" refer to RNA and DNA molecules having the same complementary base pair hybridization properties. RNA and DNA equivalents have different sugar groups (i.e., ribose versus deoxyribose), and may differ by the presence of uracil in RNA and thymine in DNA. The difference between RNA and DNA equivalents do not contribute to differences in substantially corresponding nucleic acid sequences because the equivalents have the same degree of complementarity to a particular sequence.

General Overview

The biological fitness of NA inhibitor-resistant viruses differs depending on the type of mutations in the NA. The infectivity and transmissibility of clinical isolates of human influenza A viruses carrying the Arg292Lys or the His274Tyr mutation in their NAs were compromised in mouse or ferret models (Carr et al., 2002; Herlocher et al., 2002; Ives et al., 2002; Herlocher et al., 2004) and a similar result was reported for a mutant type B virus possessing the Arg152Lys mutation in ferrets (Gubareva et al., 1998). By contrast, a resistant virus with the Glu119Val mutation infected ferrets and was transmitted among these animals as efficiently as the wild-type virus (Herlocher et al., 2004). Also, influenza B virus carrying the Asp198Asn substitution grows as well as the wild-type virus in this animal model (Mishin et al., 2005). Nonetheless, the pathogenicity and transmissibility of NA inhibitor-resistant viruses remain open questions that bear directly on pandemic strains. In Japan, the NA inhibitors zanamivir and oseltamivir were approved for clinical use in 2000 and 2001, respectively, and now are used more extensively in that country than anywhere else in the world (Ward et al., 2005; Roche, 2006).

An influenza B virus caused a widespread epidemic in Japan, created opportunities to assess the prevalence and transmissibility of influenza B viruses with reduced sensitivity to NA inhibitors in a natural setting. The results reported herein suggest a low but appreciable rate of emergence of type B viruses with reduced NA inhibitor sensitivity and their person-to-person transmission, in both the community and within single families. Moreover, substitutions at certain positions were associated with oseltamivir resistance, zanamivir resistance, or resistance to both oseltamivir and zanamivir. For example, a nonconservative substitution at position 198 or 222 in NA was associated with reduced sensitivity to a NA inhibitor. Also, a substitution of a residue with an aliphatic side chain for an aliphatic hydroxyl side chain, or a substitution of a residue with an aliphatic hydroxyl side chain for an aliphatic side chain, e.g., position 250 or 402, was associated with reduced sensitivity to NA inhibitor. Conservative amino acid substitutions include aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitutions also include groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine.

Thus, the invention provides methods to detect resistant influenza B viruses, e.g., using rapid nucleic acid based assays, and isolated NA inhibitor resistant influenza B viruses, e.g., those useful as controls in detection assays or assays to screen for inhibitors of resistant influenza B viruses.

In particular, the present methods are useful for rapid diagnosis and epidemiologic studies. For instance, a sample taken from a patient, e.g., at a clinic or hospital, is analyzed using a nucleic acid amplification reaction. The sample or a portion thereof is contacted with primers that identify a NA gene of a virus acid isolate of the invention, for instance, an isolate with one or more substitutions at residues 198, 222, 250, or 402 in NA that are associated with reduced sensitivity to an NA inhibitor, e.g., reduced sensitivity to peramivir. The primers may flank the region encoding the substitution(s) or may have a sequence corresponding to the sequence for the substitution or a sequence for corresponding to the nonsubstituted sequence. The sample or a portion thereof may also be contacted with control primers. One or more samples are then subjected to a nucleic acid amplification reaction. In one embodiment, real time PCR is employed. As a combination of NA and HA substitutions may enhance the reduced sensitivity to NA inhibitors as a result of a reduced dependency on NA activity, the amplification assay may include detecting the residue present at one or more of positions in HA, such as residues 327 or 426 in HA.

In another embodiment, an antibody that specifically recognizes a substitution at one or more of positions 198, 222, 250 or 402 in the NA that is associated with reduced sensitivity to an NA inhibitor, e.g., one raised to a peptide with that substitution, may be employed in the same setting, to detect an influenza B virus likely having reduced sensitivity to one or more NA inhibitors, e.g., via a dipstick assay.

The virus isolated of the invention may be used as a control, e.g., as a positive control in a nucleic acid amplification reaction or dipstick assay, or to assess agents for their efficacy against influenza B viruses, such as those with reduced sensitivity to NA inhibitor.

The residues associated with reduced sensitivity to a NA inhibitor are generally located near the enzymatic (active) site of NA. To address how those residues may alter entry into the active site, molecular modeling may be employed with the NA of the virus isolate of the invention. Molecular modeling refers to techniques that generate one or more 3D models of a ligand binding site or other structural feature of a macromolecule. Molecular modeling techniques can be performed manually, with the aid of a computer, or with a combination of these. For instance, visual inspection of a computer model of NA can be used, in association with manual docking of models of functional groups into its binding pockets. Software for implementing molecular modeling techniques may also be used. Typical suites of software include CERIUS, SYBYL, AMBER, HYPERCHEM, INSIGHT II, CATALYST, CHEMSITE, or QUANTA. These packages implement many different algorithms that may be used. Molecular modeling allows for the construction of structural models that can be used for in silico drug design and modeling.

Accordingly, the NA of the virus isolate of the invention may be employed in silico, e.g., to tailor (design) drugs that may inhibit influenza B viruses with a reduced sensitivity to a NA inhibitor, and/or to predict individual substitutions or combinations of substitutions that may result in increased sensitivity or resistance to NA inhibitors, which substituted NAs in turn may be used in silico to design NA inhibitors. Compounds in in silico libraries can be screened for their ability to interact with NAs by using their respective atomic co-ordinates in automated docking algorithms. An automated docking algorithm is one which permits the prediction of interactions of a number of compounds with a molecule having a given atomic structure. Suitable docking algorithms include: DOCK, AUTODOCK, MOE-DOCK or FLEXX. Docking algorithms can also be used to verify interactions with ligands designed de novo.

For instance, AutoDock, which uses a Lamarckian genetic algorithm (a hybrid of evolutionary algorithm sampling with local search methods) to search for the optimal conformation of a given ligand in relation to a target receptor structure, may be used to model drugs and a NA. AutoDock seeks the best interaction energy between a flexible ligand and a protein surface to determine a threshold at which interactions become significant. Results of different interactions, e.g., between different drugs and a specific NA or between a drug and different NAs, may be sorted by average interaction energy. A two-stage screening, involving affinity selection by docking simulation and evolution of the drug may be employed. Designation of the target area as next to the substrate-binding site of NA in the docking simulation may allow for the selection of a non-competitive inhibitor. Rounds of selection may be carried out on the computer; the distribution of the docking energy decreased gradually for each generation and improvements in the docking energy observed over the rounds of selection.

Thus, the invention also provides an in silico method for identifying a compound that interacts with a NA having reduced sensitivity to a NA inhibitor. The method includes providing atomic co-ordinates of the NA, see, for instance, the NCBI Molecule Modeling Database, such as 1NSB or 1A4G, in a storage medium on a computer. The computer is employed to apply molecular modeling techniques to the co-ordinates. In one embodiment, the coordinates are for at least one of residues 198, 222, 250, or 402 of NA, with the substitutions described herein, where the numbering for NA is that for N2.

Oligonucleotide Primers and Probes

It is not always necessary to determine the entire nucleic acid sequence of a gene of interest in order to obtain an oligonucleotide primer or probe sequence for that gene or to determine the nucleic acid sequence of that gene from a large number of sources in order to detect heterogenity. Once a particular sequence is available for a gene of interest such as one associated with viral resistance to an inhibitor, the following guidelines are useful for designing primers or probes with desired characteristics.

First, the stability of the oligonucleotide:target polynucleotide hybrid is chosen to be compatible with the assay conditions. This may be accomplished by avoiding long A and T rich sequences, by terminating the hybrids with G:C base pairs and by designing the probe in such a way that the $T_m$ will be appropriate for standard conditions to be employed in the assay (amplification or hybridization). The nucleotide sequence of the primer or probe should be chosen so that the length and % G and % C result in a probe having a $T_m$ about 2 to 10° C. higher than the temperature at which the final assay is performed. The base composition of the primer or probe is significant because G:C base pairs exhibit greater thermal stability when compared with A:T base pairs. Thus, hybrids involving complementary polynucleotides having a high G:C content are generally stable at higher temperatures when compared with hybrids having a lower G:C content.

Second, the position at which the primer or probe binds its target polynucleotide is chosen to minimize the stability of hybrids formed between probe:non-target polynucleotides. This may be accomplished by minimizing the length of perfect complementarity with polynucleotides of non-target organisms, by avoiding G:C rich regions of homology with non-target sequences, and by positioning the primer or probe to span as many destabilizing mismatches as possible. Whether a primer or probe sequence is useful for amplifying or detecting only a specific type of gene depends largely on thermal stability differences between probe:target hybrids and probe:non-target hybrids. The differences in $T_m$ should be as large as possible to produce highly specific primers and probes.

The length of the target polynucleotide sequence and the corresponding length of the primer or probe sequence also are important factors to be considered when designing a primer or probe. While it is possible for polynucleotides that are not perfectly complementary to hybridize to each other, the longest stretch of perfectly homologous base sequence is ordinarily the primary determinant of hybrid stability.

Third, regions which are known to form strong internal structures inhibitory to hybridization of a primer or probe are less preferred as targets. Primers or probes having extensive self-complementarity also should be avoided.

Once a presumptive unique sequence has been identified, corresponding oligonucleotides are produced. Defined oligonucleotides that can be used to practice the invention can be produced by any of several well-known methods, including automated solid-phase chemical synthesis using phosphoramidite precursors. Other well-known methods for construction of synthetic oligonucleotides may, of course, be employed. Oligonucleotides may be modified with chemical groups to enhance their performance. Backbone-modified oligonucleotides, such as those having phosphorothioate or methylphosphonate groups, are examples of analogs that can be used in conjunction with oligonucleotides of the present invention. These modifications render the oligonucleotides resistant to the nucleolytic activity of certain polymerases or to nuclease enzymes. Other analogs that can be incorporated into the structures of the oligonucleotides include peptide nucleic acids, or "PNAs." The PNAs are compounds comprising ligands linked to a peptide backbone rather than to a phosphodiester backbone. Representative ligands include either the four main naturally occurring DNA bases (i.e., thymine, cytosine, adenine or guanine) or other naturally occurring nucleobases (e.g., inosine, uracil, 5-methylcytosine or thiouracil) or artificial bases (e.g., bromothymine, azaadenines or azaguanines, etc.) attached to a peptide backbone through a suitable linker. PNAs are able to bind complementary ssDNA and RNA strands. Methods for making and using PNAs are disclosed in U.S. Pat. No. 5,539,082. Another type of modification that can be used to make oligonucleotides having the sequences described herein involves the use of non-nucleotide linkers (e.g., see U.S. Pat. No. 6,031,091) between nucleotides in the nucleic acid chain which do not interfere with hybridization or optionally elongation of a primer.

Yet other analogs include those which increase the binding affinity of a probe to a target nucleic acid and/or increase the rate of binding of the probe to the target nucleic acid relative to a probe without the analog. Such analogs include those with a modification (substitution) at the 2' position of a ribofuranosyl nucleotide. Analogs having a modification at the 2' position of the ribose are one embodiment. Other substitutions at the 2' position of the sugar are expected to have similar properties so long as the substitution is not so large as to cause steric inhibition of hybridization. Thus, hybridization assay probes can be designed to contain modified nucleotides which, alone or in combination, may have the advantage of increasing the rate of target-specific hybridization.

Preferably, probes are labeled. Essentially any labeling and detection system that can be used for monitoring specific nucleic acid hybridization can be used in conjunction with the probes disclosed herein when a labeled probe is desired. Included among the collection of useful labels are: radiolabels, enzymes, haptens, linked oligonucleotides, colorimetric, fluorometric, e.g., 6-carboxyfluorescein (FAM), carboxytetramethylrhodamine (TAMRA), or VIC (Applied Biosystems), or chemiluminescent molecules, and redox-active moieties that are amenable to electrochemical detection methods. In one embodiment, probes are labeled at one end with a reporter dye and with a quencher at the other end, e.g., reporters including FAM, 6-tetrachlorofluorescein (TET), MAX (Synthegen), Cy5 (Synthegen), 6-carboxy-X-rhodamine or 5(6)-carboxy-X-rhodamine (ROX), and TAMRA and quenchers including TAMRA, BHQ (Biosearch Technologies) and QSY (Molecular Probes). Standard isotopic labels that can be used to produce labeled oligonucleotides include $^3$H, $^{35}$S, $^{32}$P, $^{125}$I, $^{57}$Co and $^{14}$C. When using radiolabeled probes, hybrids can be detected by autoradiography, scintillation counting or gamma counting.

Non-isotopic materials can also be used for labeling oligonucleotide probes. These non-isotopic labels can be positioned internally or at a terminus of the oligonucleotide probe. Modified nucleotides can be incorporated enzymatically or chemically with modifications of the probe being performed during or after probe synthesis, for example, by the use of non-nucleotide linker groups. Non-isotopic labels include colorimetric molecules, fluorescent molecules, chemiluminescent molecules, enzymes, cofactors, enzyme substrates, haptens or other ligands. For instance, U.S. Pat. No. 5,998,135 discloses yet another method that can be used for labeling and detecting probes using fluorimetry to detect fluorescence emission from lanthanide metal labels disposed on probes, where the emission from these labels becomes enhanced when it is in close proximity to an energy transfer partner. Exemplary electrochemical labeling and detection approaches are disclosed in U.S. Pat. Nos. 5,591,578 and 5,770,369, and PCT/US98/12082, the disclosures of which are hereby incorporated by reference. Redox active moieties useful as electrochemical labels include transition metals such as Cd, Mg, Cu, Co, Pd, Zn, Fe and Ru. Indeed, any number of different non-isotopic labels can be used for preparing labeled oligonucleotides in accordance with the invention. For example, a probe may contain more than one label.

Alternative procedures for detecting particular sequences can be carried out using either labeled probes or unlabeled probes. For example, hybridization assay methods that do not rely on the use of a labeled probe are disclosed in U.S. Pat. No. 5,945,286 which describes immobilization of unlabeled oligonucleotide probe analogs made of peptide PNAs, and detectably labeled intercalating molecules which can bind double-stranded PNA probe/target nucleic acid duplexes. In these procedures, as well as in certain electrochemical detection procedures, such as those disclosed in PCT/US98/12082, PCT/US98/12430 and PCT/US97/20014, the oligonucleotide probe is not required to harbor a detectable label.

Nucleic acid primers and probes specific for a drug resistance gene, optionally in combination with one or more probes specific for an organism, or a different gene in that organism, find use in an assay to detect the presence of the gene of interest in nucleic acid from a biological sample and optionally to identify an organism and/or to ensure that the nucleic acid in the sample is adequate to detect the gene of interest (i.e., an internal control).

Antiviral Resistance Gene Primers and Probes

Antiviral resistance complicates treatment and often leads to therapeutic failures. Furthermore, overuse of antivirals may lead to the emergence of viral resistance. Besides the rapid identification of negative clinical specimens with DNA-based tests for viral detection and the identification of the presence of a virus in the positive specimens, the clinician also needs timely information about the ability of the virus to resist treatments.

By examining partial or complete sequences of NA genes of various influenza virus isolates, aligning those sequences with structurally and/or functionally related sequences to reveal areas of maximum homology and areas of sequence variation, sequences can be identified that are conserved among NA genes but exhibit mismatches with structurally and/or functionally related genes. In particular, primers and probes that preferentially anneal to a nucleic acid target region and can initiate nucleic acid synthesis and/or form a detectable duplex that indicates the presence of a NA gene with a particular sequence, are chosen for polynucleotide-based diagnostic assays.

One method for detecting the presence of a NA gene with a particular sequence, includes the step of contacting a test sample with at least two oligonucleotide primers under conditions that preferentially amplify NA sequences. Alternatively, a test sample is contacted under high stringency hybridization conditions with at least one oligonucleotide probe that preferentially hybridizes to selected NA sequences.

While oligonucleotides probes of different lengths and base composition may be used for detecting the NA gene, oligonucleotides may have lengths from 10 up to 40 nucleotides, e.g., 10 to 20 nucleotides, and are sufficiently homologous to the target nucleic acid to permit amplification of a NA template and/or hybridization to such a template under high stringency conditions. The probes may include sequences unrelated to the NA gene, for instance at the 5' end, the 3' end, or both the 5' and 3' ends. Likewise, primers may include sequences unrelated to the NA gene, e.g., at the 5' end. Preferred primers and probes have sequences of up to 40 nucleotides in length and preferably have at least 10 contiguous nucleotides corresponding to selected sequences in the NA gene. Preferred oligonucleotide sequences include RNA and DNA equivalents, and may include at least one nucleotide analog.

The primers and probes are tested against synthetic targets as well as tested against biological samples, in an amplification and/or hybridization reaction so as to detect a particular NA gene. In one method of determining whether a biological sample contains certain NA gene sequences, nucleic acids are released from cells or virions in a biological sample by addition of a lysing agent, e.g., a detergent, or by other known methods for disrupting cells including the use of enzymes, osmotic shock, heat, chemical treatment, and vortexing, for instance, with glass beads, or sonic disruption, for example according to the method disclosed in U.S. Pat. No. 5,374,522. Methods suitable for liberating nucleic acids which can then be subjected to hybridization methods have been described in U.S. Pat. No. 5,837,452 and in U.S. Pat. No. 5,364,763.

Preferably, the probes specifically hybridize to NA nucleic acid only under conditions of high stringency. Hybrids will not form in the absence of a sufficient degree of complementarity. Accordingly, the stringency of the assay conditions determines the amount of complementarity needed between two nucleic acid strands forming a hybrid. Stringency is chosen to maximize the difference in stability between the hybrid formed with target nucleic acid and non-target nucleic acid.

Amplification and Hybridization

Amplification or hybridization assays may be performed either in tubes or in microtitration plates having multiple wells. For assays in plates, the wells may be coated with the specific amplification primers or probes and/or control DNAs, and the detection of amplification products or the formation of hybrids may be automated. Hybridization assays may also be performed on a solid substrate.

A. Amplification

Cells or noncellular samples are subjected to conditions which release polynucleotides from the cells, thus forming an extract. For example, samples may be treated with detergents, base and/or heat denatured. If the base is employed, the mixture is then neutralized with an acidic composition. Then reagents are added to yield an amplification reaction (containing, for example, monovalent ions, detergent, dNTPS, primers, and a polymerase).

For DNA amplification by the widely used PCR (polymerase chain reaction) method, primer pairs may be derived from sequenced DNA fragments from clinical samples or from data bank sequences. Prior to synthesis, the potential primer pairs may be analyzed by using the program Oligo™ 4.0 (National Biosciences) to verify that they are likely candidates for PCR amplifications. A select set of primers can then be tested in PCR or other amplification-based assays performed directly from a suspension or a known standard to determine their specificity.

During DNA amplification by PCR, two oligonucleotide primers binding respectively to each strand of a denatured double-stranded cDNA derived from the viral genome are used to amplify exponentially in vitro the target DNA by successive thermal cycles allowing denaturation of the DNA, annealing of the primers and synthesis of new targets at each cycle. An exemplary PCR protocols is as follows. Clinical specimens or isolated virus preparations are added directly to the 50 μL PCR reaction mixtures containing 50 mM KCl, 10 mM Tris-HCl pH 8.3, 2.5 mM $MgCl_2$, 0.4 μm of each of the two primers, 200 μM of each of the four dNTPs and 1.25 Units of Taq DNA polymerase (Perkin Elmer). PCR reactions are then subjected to thermal cycling (3 minutes at 95° C. followed by 30 cycles of 1 second at 95° C. and 1 second at 55° C.) using a Perkin Elmer 480™ thermal cycle and subsequently analyzed by standard ethidium bromide-stained agarose gel electrophoresis. It is clear that other methods for the detection of specific amplification products, which may be faster and more practical for routine diagnosis, may be used. Such methods may be based on the detection of fluorescence after amplification (e.g. TaqMan™ system from Perkin Elmer or Amplisensor™ from Biotronics) or other labels such as biotin (SHARP Signal™ system, Digene Diagnostics), or liquid or solid phase hybridization with an oligonucleotide probe binding to internal sequences of the specific amplification product, e.g., a labeled probe. Methods based on the detection of fluorescence are very rapid and quantitative, and can be automated. For instance, one of the amplification primers or an internal oligonucleotide probe specific to the amplicon(s) is coupled with the fluorochrome or with any other label. Moreover, methods based on the detection of fluorescence are particularly suitable for diagnostic tests since they are rapid and flexible as fluorochromes emitting different wavelengths are available (Perkin Elmer). Further, a variety of fluorochromes emitting at different wavelengths, each coupled with a specific oligonucleotide linked to a fluorescence quencher which is degraded during amplification, thereby releasing the fluorochrome (e.g., TaqMan™, Perkin Elmer), may be employed.

To assure PCR efficiency, glycerol or dimethyl sulfoxide (DMSO) or other related solvents, can be used to increase the sensitivity of the PCR and to overcome problems associated with the amplification of target with a high GC content or with strong secondary structures. The concentration ranges for glycerol and DMSO are 5 to 15% (v/v) and 3 to 10% (v/v), respectively. For the PCR reaction mixture, the concentration ranges for the amplification primers and the $MgCl_2$ are about 0.1 to 1.0 and 1.5 to 3.5 mM, respectively. Modifications of the standard PCR protocol using external and nested primers (i.e., nested PCR) or using more than one primer pair (i.e., multiplex PCR) may also be used (Persing et al, 1993), for instance, to detect simultaneously several genes, including NA inhibitor resistance genes and genes useful to identify the type of influenza virus.

The person skilled in the art of DNA amplification knows the existence of other rapid amplification procedures which include linear amplification procedure, e.g., ligase chain reaction (LCR), transcription-based amplification systems (TAS), self-sustained sequence replication (3SR), nucleic acid sequence-based amplification (NASBA), strand displacement amplification (SDA) and branched DNA (bDNA). The scope of this invention is not limited to the use of amplification by PCR, but rather includes the use of any rapid nucleic acid amplification methods or any other procedures which may be used to increase rapidity and sensitivity of the tests. Any oligonucleotides suitable for the amplification of specific nucleic acid sequences by approaches other than PCR and within scope of this invention.

Standard precautions to avoid false positive PCR results should be taken. Methods to inactivate PCR amplification products such as the inactivation by uracil-N-glycosylase may be used to control PCR carryover. For example, in the case of direct amplification, a portion of the sample may be transferred directly to a 50 μL PCR reaction mixture (e.g., containing 50 mM KCl, 10 mM Tris pH 8.3, 2.5 mM $MgCl_2$, 0.4 μM of each of the two primers, 200 μM of each of the four dNTPs and 1.25 Unit of Taq DNA polymerase (Perkin Elmer)). The reaction mixture is overlaid with 50 μL of mineral oil and PCR amplifications are carried out for instance using an initial denaturation step of 3 minutes at 95° C. followed by 30 cycles consisting of a 1 second denaturation step at 95° C. and of a 1 second annealing step at 55° C. in a Perkin Elmer 480™ thermal cycler. PCR amplification products can be analyzed by standard agarose gel (2%) electrophoresis. Amplification products are visualized in agarose gels containing 2.5 μg/mL of ethidium bromide under UV at 254 nm. The entire PCR assay can be completed in approximately one hour.

Alternatively, amplification may be performed as described above but using a "hot start" protocol. In that case, an initial reaction mixture containing the target DNA, primers and dNTPs was heated to about 85° C. prior to the addition of the other components of the PCR reaction mixture. The final concentration of all reagents was as described above. Subsequently, the PCR reactions were submitted to thermal cycling and analysis as described above.

To eliminate the PCR inhibitory effects of clinical specimens, samples may be diluted in lysis buffer containing detergent(s). Subsequently, the sample is added directly to the PCR reaction mixture. Heat treatment of the samples, prior to DNA amplification, using the thermocycler or a microwave oven may also be performed. PCR has the advantage of being compatible with crude DNA preparations. Thus, samples such as blood, cerebrospinal fluid, and nasopharyngeal samples, may be used directly in PCR assays after a brief heat treatment.

B. Hybridization

In hybridization experiments, oligonucleotides (of a size less than about 100 nucleotides) have some advantages over DNA fragment probes of greater than 100 nucleotides in length for the detection of bacteria such as ease of preparation in large quantities, consistency in results from batch to batch and chemical stability. The oligonucleotide probes may be derived from either strand of the target duplex DNA. The probes may consist of the bases A, G, C, or T or analogs thereof. In one embodiment, the target DNA is denatured, fixed onto a solid support and hybridized with a DNA probe. Conditions for pre-hybridization and hybridization can be as follows: (i) pre-hybridization in 1 M NaCl+10% dextran sulfate+1% SDS (sodium dodecyl sulfate)+1 µg/ml salmon sperm DNA at 65° C. for 15 minutes, (ii) hybridization in fresh pre-hybridization solution containing the labeled probe at 65° C. overnight, and (iii) post-hybridization including washing twice in 3×SSC containing 1% SDS (1×SSC is 0.15 M NaCl, 0.015 M NaCitrate) and twice in 0.1×SSC containing 0.1% SDS; all washes at 65° C. for 15 minutes. For probes labeled with radioactive labels, the detection of hybrids is preferably by autoradiography. For non-radioactive labels, such as probes having colorimetric, fluorescent or chemiluminescent labels, target DNA need not be fixed onto a solid support.

For example, stringent conditions are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% sodium dodecylsulfate (SDS), and 10% dextran sulfate at 42° C., with washes at 42° C. in 0.2×SSC and 0.1% SDS. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3.

Results from an amplification and/or probe hybridization reaction can be inputted into a computer or data processor ("computer"), either manually using a keyboard or directly through an interface from an automated device such as a plate reader, film scanner or luminometer. The computer can sort the positive and negative results for a particular sample to establish a profile be compared with a look-up table stored in a memory device linked to the computer to associate the profile with results obtained using control organisms in order to determine the presence or absence of a gene of interest in the test organism. Thus, one or more NA probes can be used to identify the NA status of a sample. Of course, a series of positive and negative control hybridizations can be carried out in parallel to ensure validity of the testing results.

Methods to detect polymorphisms in nucleic acid samples are known, see, e.g., U.S. Pat. Nos. 6,235,889, 5,843,652, 7,141,658, 7,175,985, 7,160,680, 7,056,740, 7,018,816, 6,878,530, 6,825,010, 6,821,733, 6,770,443, 6,750,022, 6,727,063, 7,109,316, 6,986,992, 6,972,714, 6,884,584, and 6,682,887. For instance, primers flanking the sequence of interest are employed to amplify nucleic acid in the region of the sequence of interest, and then differentially labeled probes specific for different (missense) sequences employed. For example, probes may have a fluorescent dye at one end, and optionally a fluorescent quencher at the other, and also optionally a minor groove binder for use with shorter probes, for real-time quantitative PCR.

The invention will be further described by the following nonlimiting examples.

EXAMPLE 1

Methods

Study Population and Settings

To identify the frequency of developing NA inhibitor-resistant influenza B viruses after oseltamivir therapy, at least two clinical specimens from pediatric patients, one taken at the initial hospital visit (pretreatment samples) and the other during treatment with oseltamivir (posttreatment samples), were analyzed. Pharyngeal or nasal swabs were obtained for influenza B virus analysis from patients who visited the pediatric services at four community hospitals during the influenza season. Patients who were positively diagnosed with influenza B virus infection by a rapid diagnostic kit and received oseltamivir therapy, and from whom at least two sequential samples were obtained for virus isolation, were enrolled in the first series of studies (FIG. 1). In the second series of studies, the prevalence of influenza B viruses with reduced sensitivity to NA inhibitors was assessed in a community setting. To this end, samples were obtained before oseltamivir treatment from patients who visited the above-mentioned facilities. The influenza B viruses isolated from these samples and the viruses from the pretreatment samples from the first series of studies were combined and analyzed (FIG. 1). Because these studies include patients who visited community hospitals, several family members sought consultation at the same facility.

Informed consent was obtained from the parents of all patients. This study was conducted with the approval of the ethics committees of the hospitals. In the case of a medical facility in which an ethics committee did not exist, the activities of the study were undertaken under the auspices of the informed consent.

Clinical Specimens and Viruses

Pharyngeal or nasal swabs for influenza B virus isolation were obtained by attending physicians after informed consent was obtained. The viruses isolated were stored at −80° C. until used. The viral isolates were used as mixed populations without plaque purification. Madin-Darby canine kidney (MDCK) cells overexpressing the β-galactoside α2,6-sialyltransferase I (ST6Gal I) gene (Hatakeyama et al., 2005) were used for viral isolation and plaque assay. These cells support the growth of clinical isolates of human influenza viruses better than unmanipulated MDCK cells. To assess the sensitivity of the influenza B viruses to NA inhibitors, the concentration of NA inhibitor required to inhibit 50% of the NA sialidase activity of the viruses ($IC_{50}$) was determined with pre- and posttreatment influenza β isolates using a sialidase inhibition assay (Hatakeyama et al., 2005; Gubareva et al., 2001). The $IC_{50}$ values demonstrated in this study were assessed for viruses present in culture supernatant fluids without plaque purification of the isolates. For strains demonstrating reduced susceptibility to the inhibitors, their NA and hemagglutinin (HA) genes were sequenced.

Sialidase Sensitivity to NA Inhibitors

Sialidase sensitivities of influenza B viruses to NA inhibitors were evaluated with a sialidase inhibition assay as described in Hatakeyama et al. (2005) and Gubareva et al. (2001). Briefly, 2'-(4-methylumbelliferyl)-α-D-N-acetylneuraminic acid (MUNANA; Sigma, St. Louis, Mo., USA) at a final concentration of 0.1 mmol/L was used as a substrate. Ten μl of the virus dilution (predetermined to contain sialidase activity in the range of 800-1200 fluorescence units in this assay) and 10 μl of the NA inhibitor (0.01 mol/L to 10 μmol/L) in calcium-MES buffer (33 mmol/L 2-[N-morpholino]ethanesulfonic acid, 4 mmol/L $CaCl_2$, pH 6.0) were mixed and incubated at 37° C. for 30 minutes, followed by the addition of 30 μL of the substrate. The mixtures were further incubated at 37° C. for 60 minutes, and the reaction was stopped by adding 150 μl of 0.1 mol/L sodium hydroxide in 80% ethanol (pH 10.0). Fluorescence was quantified at an excitation wavelength of 360 nm and an emission wavelength of 465 nm. The $IC_{50}$ value was determined by extrapolation of the relation between the concentration of inhibitor and the proportion of fluorescence inhibition. Results are reported as the mean of duplicate $IC_{50}$ values. Oseltamivir carboxylate (GS4071; Roche Products, Basel, Switzerland), the active metabolite of the ethyl ester pro-drug oseltamivir phosphate, and zanamivir (Relenza; GlaxoSmithKline, Brentford, UK) were used as NA inhibitors.

Sequence Analyses of the HA and NA Genes

Viral RNA was extracted from virus in cell-culture supernatant fluid with an RNA extraction kit (ISOGEN-LS; Nippon Gene, Tokyo, Japan), without prior plaque purification of the virus. Reverse transcription was performed with reverse transcriptase (SUPERSCRIPT III; Invitrogen, Carlsbad, Calif., USA) and a primer complementary to the 3' end of the viral RNA (5'-AGCAGAAGCAGAGCA-3'; SEQ ID NO:1). The cDNA products were then used to amplify the viral NA and HA genes by a standard PCR method (Pfu Ultra DNA Polymerase; Stratagene, La Jolla, Calif., USA). The primer sequences and amplification conditions were as described in FIG. 7. PCR products were cloned into the pCRBlunt II-TOPO vector (Invitrogen) and transformed them into TOP10 chemically competent cells (Invitrogen). Transformed cells were grown on Luria broth agar containing 50 mg/L kanamycin, after which the kanamycin-resistant colonies were selected and incubated in Luria broth at 37° C. overnight in a shaking incubator. Plasmid DNA was extracted with the MagExtractor-plasmid system (TOYOBO, Osaka, Japan). The complete sequences of the NA and HA genes were determined by cycle sequencing with dye-terminator chemistry (Big Dye; Applied Biosystems, Foster City, Calif., USA) on the Applied Biosystem 3100 or 3130X1 Auto Sequencer using M13F-20, NA-specific, or HA-specific primers. Five to eight cDNA clones of the NA and HA genes were analyzed for each sample.

Results

Study Population

A total of 75 pairs of pre- and posttreatment samples were obtained from pediatric patients. One sample pair was excluded because influenza virus was not isolated from either pre- or posttreatment sample. Thus, 74 patients with influenza B virus infection, aged 0-15 years (median, 3 years), were enrolled in the study (FIG. 1). All were treated with oseltamivir for 5 days. Eighteen children received 2 mg/kg body weight twice daily, while the remaining 56 children received weight-based unit doses (Gubarev et al., 2001) (body weight ≦15 kg, 30 mg twice daily; >15-23 kg, 45 mg twice daily; >23-40 kg, 60 mg twice daily; >40 kg, 75 mg twice daily). In the second series of experiments, a total of 442 influenza B viruses isolated from patients prior to treatment (348 patients plus above mentioned 74 patients) during the influenza season (FIG. 1) was analyzed. Of the 422 patients, 356 were children aged 0-15 years (median, 5 years) and the remaining 66 were adults aged 16 or older (ranged from 17 to 61 years; median, 34 years).

Emergence of Influenza B Viruses with Reduced Sensitivity to NA Inhibitors after Oseltamivir Treatment Viruses were recovered from all of the pretreatment samples and 65 posttreatment samples collected from the 74 children who had received a full course of oseltamivir. In one case (1.4%), the $IC_{50}$ value of the posttreatment isolate tested against zanamivir and oseltamivir increased by 7.1-fold and 3.9-fold, respectively, compared to results for the virus isolated before treatment (Table 1; patient 1). This child was an immunocompetent 7-year-old boy who had received oseltamivir immediately after diagnosis. The virus with reduced sensitivity to the NA inhibitors was isolated from a pharyngeal swab collected on day 3 after the initiation of oseltamivir therapy. To understand the molecular basis of the observed reduced sensitivity to the drugs, the NA gene from the virus exhibiting this property was molecularly cloned. The sequence analysis revealed an amino acid substitution, Gly402Ser, in seven of the eight cDNA clones of the NA gene. No other difference was observed in the amino acid sequence of the NA and HA proteins between the wild-type parent and the posttreatment mutant virus. The NA mutation Gly402Ser was located near the sialidase enzymatic center.

Figure 2:
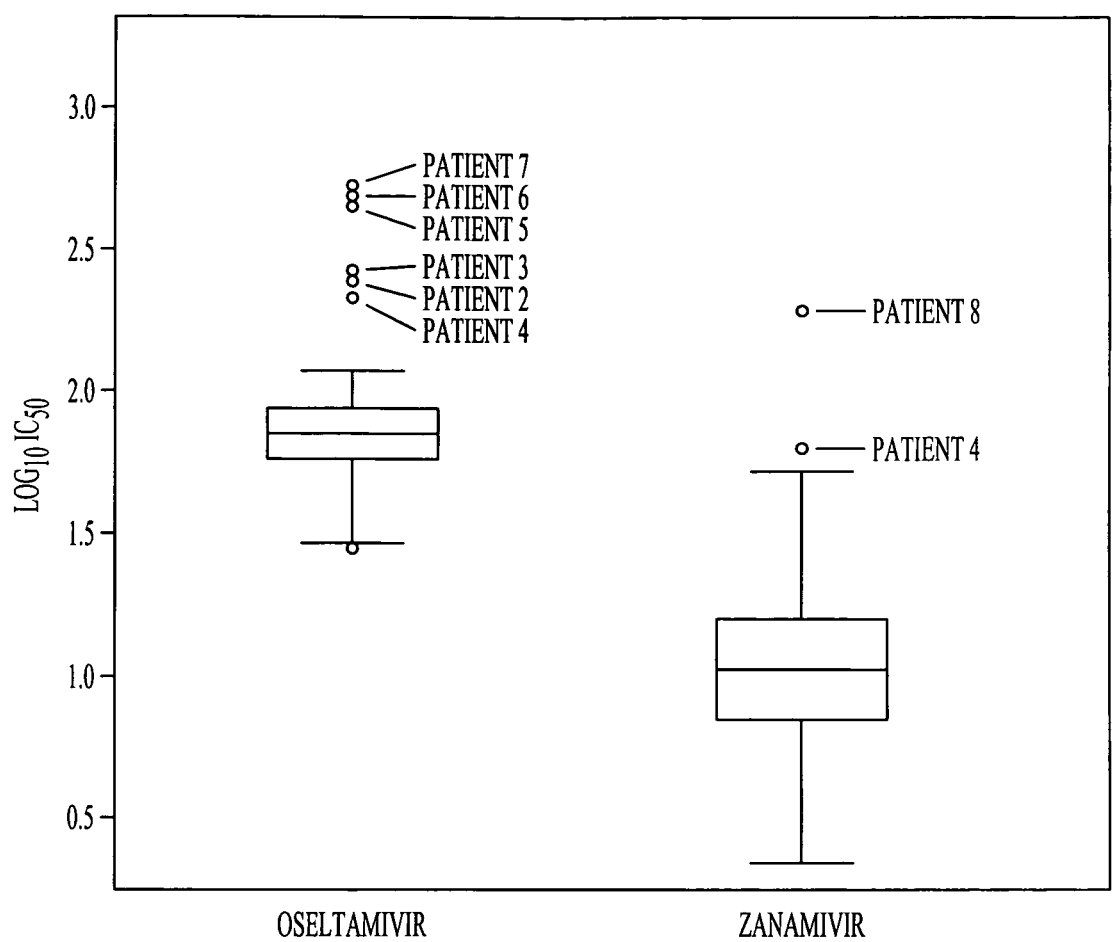
FIG. 2. Box plots of the $\log_{10}$ of the $IC_{50}$ values for influenza B viruses isolated from 422 untreated patients tested against zanamivir and oseltamivir carboxylate. The $IC_{50}$ values were determined by the sialidase inhibition assay (Hatakeyama et al., 2005; Gubareva et al., 2001). A box and the horizontal line within the box indicate the $25^{th}$-$75^{th}$ percentiles and median of the logs, respectively. Bars above and below the boxes indicate minimum and maximum values within the 1.5 times interquartile range (IQR). Open circles represent extreme values that lie outside the 1.5 times IQR. The median (IQR) $IC_{50}$ values of the 422 type B viruses from patients before treatment were 70.5 (55.8-85.1) nmol/L for oseltamivir and 10.1 (7.0-15.8) nmol/L for zanamivir.

Influenza B Viruses with Reduced Susceptibility to NA Inhibitors Detected in Patients Prior to Treatment The median (interquartile range:IQR) $IC_{50}$ values for influenza B viruses isolated from 422 untreated patients during the 2004-2005 influenza season and tested against both oseltamivir and zanamivir with the sialidase inhibition assay were 70.5 (55.8-85.1) nmol/L and 10.1 (7.0-15.8) nmol/L, respectively (FIG. 2). Considering the level of increase in the $IC_{50}$ value of the virus from the posttreatment sample as compared with that of the original virus obtained before oseltamivir therapy from patient 1, viruses whose log $IC_{50}$ values were higher than 1.5 times IQR above the third quartile were regarded as drug-resistant (FIG. 2). Using this criterion, seven (1.7%) of the 422 influenza B viruses isolated from untreated patients (Table 1, patients 2-8) were found to have reduced sensitivity to oseltamivir, zanamivir, or both drugs. Each of the seven isolates with reduced sensitivity contained amino acid substitutions in the NA at the sialidase active center, by comparison with the consensus type B NA sequence: three had Asp198Asn mutations, three Ile222Thr, and one Ser250Gly mutation (Table 1). None of these patients had an underlying disease and none had received immunosuppressive drugs.

TABLE 1

Influenza B isolates with reduced sensitivity to NA inhibitors before or after antiviral treatment

| Patient | Age and gender | Sample | IC$_{50}$ value (nmol/L) zanamivir | IC$_{50}$ value (nmol/L) oseltamivir | Mutations found in NA* | Comments |
|---|---|---|---|---|---|---|
| 1 | 7 yr, M | Pretreatment | 6.6 | 72.3 | None | A |
|  |  | Posttreatment | 46.9 | 280.6 | Gly402Ser |  |
| 2 | 8 yr, M | Pretreatment | 47.4 | 237.3 | Asp198Asn | B |
|  |  | Posttreatment | 42.2 | 228.2 | Asp198Asn |  |
| 3 | 1 yr, F | Pretreatment | 48.9 | 255.3 | Asp198Asn | Sister of patient 2 |
|  |  | Posttreatment | 51.3 | 239.7 | Asp198Asn |  |
| 4 | 6 yr, F | Pretreatment | 61.7 | 204.2 | Asp198Asn | C |
| 5 | 6 yr, M | Pretreatment | 23.3 | 443.0 | Ile222Thr | B |
| 6 | 3 yr, F | Pretreatment | 29.5 | 479.9 | Ile222Thr | Sister of patient 5 |
| 7 | 5 yr, M | Pretreatment | 22.6 | 513.8 | Ile222Thr | B |
| 8 | 22 yr, F | Pretreatment | 191.3 | 48.6 | Ser250Gly | B |

*Amino acid differences were identified by comparison with the consensus sequence of currently circulating type B viruses. Amino acid numbering was adapted to that of the N2 NA. Positions 198, 222, 250, and 402 in N2 NA correspond to positions 197, 221, 249, and 407, respectively, in type B NA.
A. Patient 1 received oseltamivir for 5 days.
B. Onset of symptoms was not preceded by infection of other family members.
C. 4-year-old sister of this patient received oseltamivir for 5 days for wild-type influenza B virus infection, but virus isolation after oseltamivir therapy was not carried out.

Figure 3:
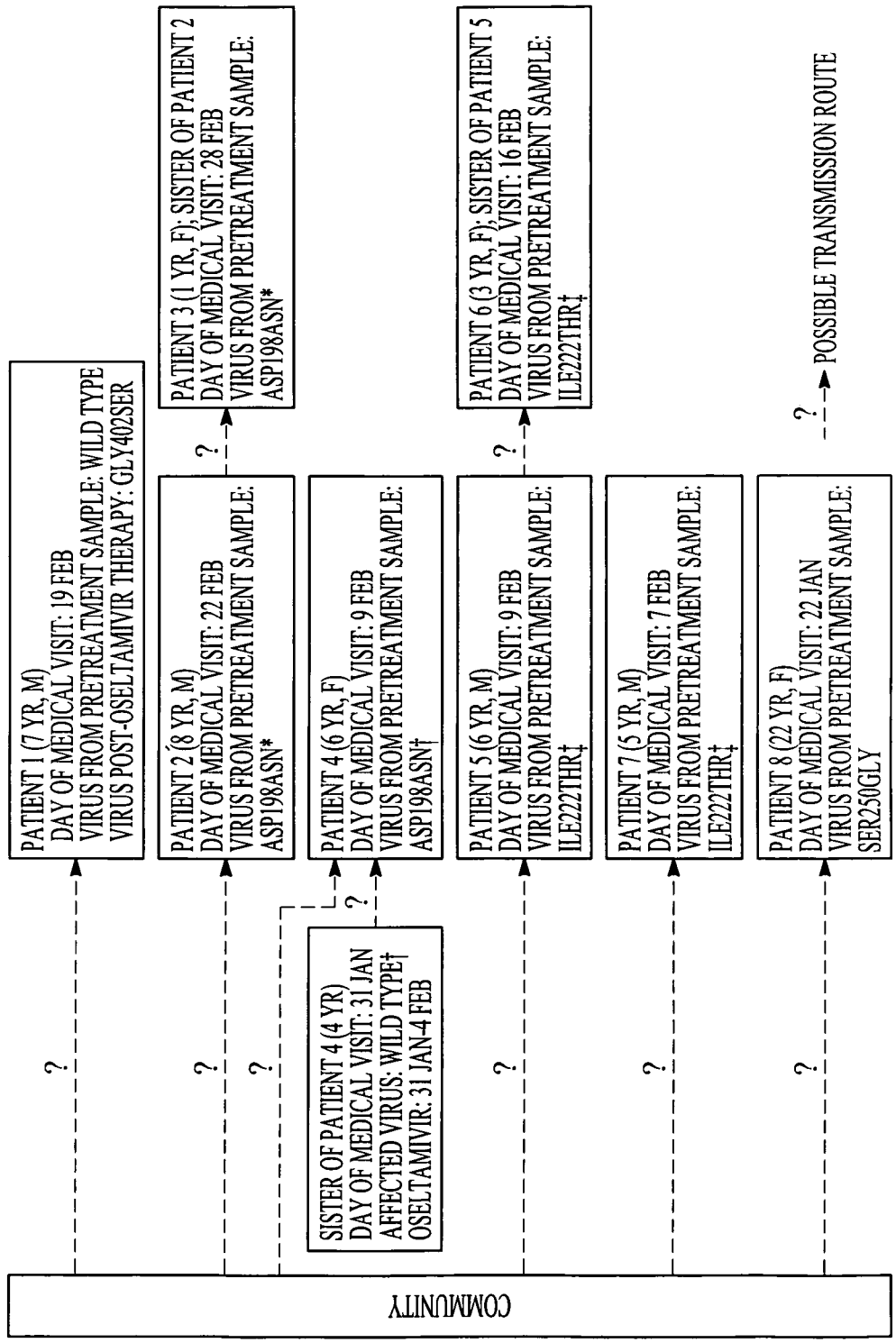
FIG. 3. Patients who shed influenza B viruses with reduced sensitivity to NA inhibitors. The variant with the Gly402Ser NA mutation was isolated from patient 1 on day 3 after the initiation of oseltamivir therapy. Patients 2, 3, and 4 were infected with variants with the Asp198Asn NA mutation, and the nucleotide sequences of the HA and NA genes of viruses from patients 2 and 3 (siblings) were identical, but were different from those of patient 4 by three and two nucleotides, respectively. Patients 5, 6, and 7 were infected with variants with the Ile222Thr NA mutation, and the HA and NA nucleotide sequences of the viruses from patients 5 and 6 (siblings) and patient 7 were identical. The virus carrying Ser250Gly NA mutation with reduced sensitivity to zanamivir was isolated from patient 8. None of the family members of patients 2, 5, 7, and 8 were affected by influenza B virus before their onset of symptoms. Possible transmission routes are indicated by broken arrows. * Nucleotide sequences of the NA and HA genes were identical between viruses isolated from the siblings. † Nucleotide sequences of the NA and HA genes were identical with the exception of the NA substitution at amino acid position 198. ‡ Nucleotide sequences of the NA and HA genes were identical between these viruses.

An 8-year-old boy (patient 2) was diagnosed with influenza B virus infection 6 days before the onset of influenza B infection in his 1-year-old sister (patient 3) (FIG. 3). The IC$_{50}$ values for the pretreatment isolate from patient 2 (237.3 nmol/L for oseltamivir and 47.4 nmol/L for zanamivir) indicated reduced sensitivity of the isolate to these compounds. An NA mutation was identified at position 198 (Asp198Asn) in all of the eight cDNA clones of the NA gene of this isolate. The virus isolated from patient 3 also showed reduced sensitivity to oseltamivir and zanamivir (Table 1). Sequence analyses of the NA and HA genes were identical between viruses isolated from patients 2 and 3, including the presence of an Asp198Asn mutation in the NA protein (in all of the eight cDNA clones of the NA gene of the isolate from patient 3). Thus, it may be possible that patient 2 was infected with an influenza B virus having reduced sensitivity to NA inhibitors, and then transmitted the virus to his sister, patient 3.

Another influenza B virus possessing the Asp198Asn mutation in the NA was isolated from patient 4 (6-year old, F) before oseltamivir treatment (Table 1; FIG. 3). This NA mutation was observed in all of the seven cDNA clones of this isolate. Her 4-year-old sister, from whom a wild-type influenza B virus was isolated, had received oseltamivir from the day of isolation and 4 additional days (Table 1; see footnote C). The sequences of both the NA and HA genes from the two patients were identical with the exception of an NA substitution at amino acid position 198. Thus, it is possible that a drug-resistant virus might have arisen in the 4-year-old sister during oseltamivir therapy and was transmitted to patient 4. However, samples after oseltamivir therapy from the 4-year-old sister were not available to confirm this.

The IC$_{50}$ values for the Asp198Asn mutants ranged from 204 to 255 nmol/L (oseltamivir) and from 42 to 62 nmol/L (zanamivir), indicating that the mutation was associated with approximately 3-4-fold and 4-6-fold reductions in drug sensitivity compared with the corresponding median IC$_{50}$ values for the entire group of type B viruses. The variant with reduced sensitivity to oseltamivir with the Asp198Asn mutation was recently identified by Gubareva et al. (2004; 2005) in a posttreatment sample from an immunocompromised child with influenza B virus, further supporting the notion that this mutation was introduced during oseltamivir therapy and that it reduced sensitivity to the NA inhibitors.

Several type B viruses carrying other NA mutations with reduced sensitivity were also identified in other patients. Viruses carrying an Ile222Thr mutation were isolated from pretreatment samples of three patients: patients 5 and 6 (siblings) and patient 7 (Table 1; FIG. 3). The nucleotide sequences of the NA and HA genes of isolates from these patients were identical, and the NA Ile222Thr mutation was observed in all of the cDNA clones of each viral NA gene. The IC$_{50}$ values for viruses carrying the Ile222Thr mutation ranged from 443 to 514 nmol/L (oseltamivir), representing a 6-7-fold reduction in sensitivity compared with the median IC$_{50}$ values for type B viruses (Table 1). This mutation appeared to lack strong impact on viral sensitivity to zanamivir. An influenza B virus with reduced sensitivity to the NA inhibitors was also isolated from patient 8, a 22-year-old female (Table 1; FIG. 3). The isolate from patient 8 possessed a Ser250Gly mutation in all of the seven cDNA clones of the NA gene. The Ser250Gly mutation conferred about 19-fold resistance to zanamivir (when compared with the median type B virus IC$_{50}$ value) but did not reduce sensitivity to oseltamivir.

None of the family members of patients 2, 5, 7, and 8 were affected by influenza B virus before onset of their symptoms, suggesting that they were possibly infected with mutants with reduced drug sensitivity circulating in the community. These results suggest that influenza B viruses with reduced sensitivity to NA inhibitors might possibly be transmitted from person to person, not only within single families, but also among members of the same community.

Finally, no appreciable differences were observed in the clinical course of viral infection between patients infected with wild-type viruses or those with reduced sensitivity to NA inhibitors. Mean durations of fever after antiviral therapy were 2.4, 2.6, and 2.0 days in patients infected with wild-type viruses (n=32), those infected with reduced sensitivity to NA inhibitors (patient 2, 3 days; patient 3, 5.5 days; patient 7, 1 day; patient 8, 1 day), and the patient with the variant that developed during therapy (patient 1), respectively. Similarly, no appreciable difference was observed in the extent of virus shedding (duration and titer) between patients infected with a drug-resistant virus and those infected with a drug-sensitive virus. However, the number of patients infected with viruses with reduced drug sensitivity is too small to assess the statistical significance of the effect of drug resistance on virus shedding.

Comment

It was demonstrated that influenza B viruses with reduced sensitivity to NA inhibitors can emerge during routine therapy and that such mutants appear to be transmitted from person to person, not only within the same family but possibly through community contacts as well. The rate of generation of influenza B viruses with reduced drug sensitivity during oseltamivir treatment in this study, 1.4%, is lower than that seen among influenza A viruses (5.5-18%) (Ward et al., 2005; Kiso et al., 2004; Whitley et al., 2001). This discrepancy could reflect the higher doses of oseltamivir used in our study (76% of the patients received weight-based unit doses of the drug, in contrast to the twice daily 2 mg/kg dose uniformly administered in previous Japanese studies (Ward et al., 2005; Kiso et al., 2004).

Figure 4:
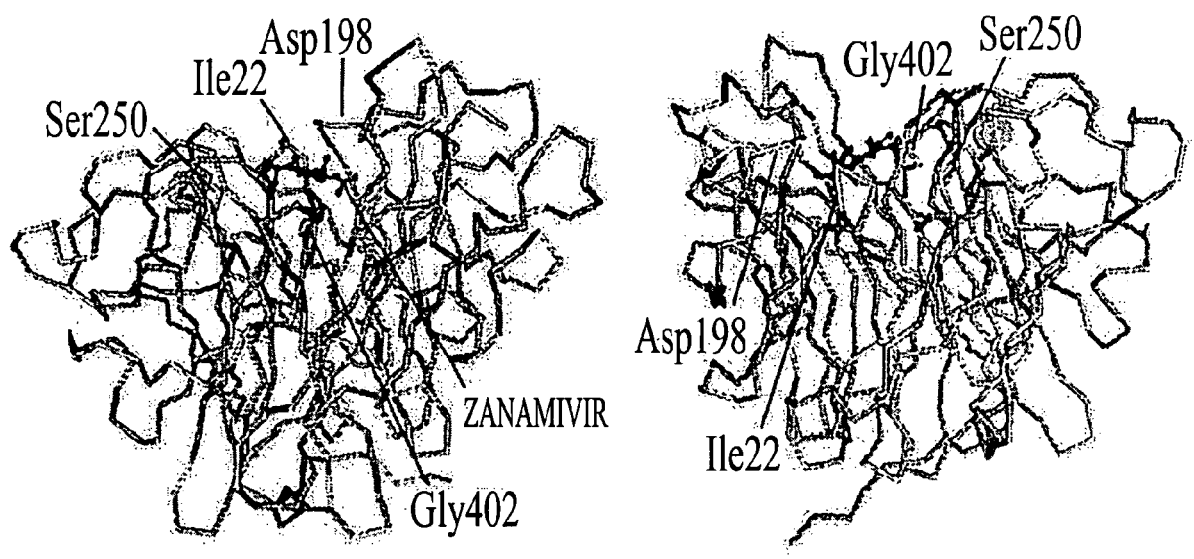
FIG. 4. Locations of mutated residues on the three-dimensional structure of NA. The three-dimensional structure of the complex between influenza virus B/Beijing/1/87 neuraminidase and zanamivir (MMDB ID: 10147, displayed with the Cn3D software). Schematic representations of a single monomer viewed from different lateral angles are shown. The NA residues addressed in the present study (Asp198, Ile222, Ser250, and Gly402; N2 numbering) are marked in yellow. The residues that are associated with reduction of drug sensitivity are located at or near the sialidase active center, where NA inhibitors bind.

Four mutations in the type B NA reduced sensitivity to NA inhibitors: Asp198Asn, Ile222Thr, Ser250Gly and Gly402Ser substitutions. Residues 198, 222, 250 are located in the framework of the NA active site, which interacts with the catalytic residues by hydrogen bonds or salt bridges (FIG. 4) (Colman et al. 1993; Burmeister et al., 1992). The framework residues Asp198 and Ser 250 (corresponding residue in the type A NA is Ala) interact with the catalytic residues Arg152 and Arg224, respectively, and Ile222 forms a hydrophobic pocket into which the substrate fits (Burmeister et al., 1992). The substitution detected in the NA of a virus recovered from an oseltamivir-treated patient in this study occurred at residue 402. Although Gly402 is not a catalytic or framework residue, it is located near the sialidase enzymatic center (FIG. 4). Therefore, Gly402Ser substitution may alter the interaction of the enzymatic center and the NA inhibitors, resulting in reduced drug sensitivity.

The framework mutations identified herein appear to reduce oseltamivir sensitivity at a moderate level as compared to the catalytic Arg292Lys mutation. The $IC_{50}$ values for H3N2 viruses with the framework mutation Glu119Val or Asn294Ser, tested against oseltamivir, were 239 nmol/L or 106 nmol/L (Kiso et al., 2004), respectively, while that for an $H5N_1$ strain with framework mutation His274Tyr was 763 nmol/L (Lee et al., 2005). On the other hand, the catalytic Arg292Lys mutation in N2 viruses conferred a high level of resistance to oseltamivir (>10,000 nmol/L) (Kiso et al., 2004). Viruses with framework mutations might have the ability to be transmitted among experimental animals, as has been shown with type A variants with a framework mutation at position 119 or 274 (Herlocher et al., 2004). These results suggest that influenza viruses with a framework mutation in the NA might be of clinical concern, even though their $IC_{50}$ values are lower than those of viruses with mutations in the catalytic domain. Thus, recent reports of oseltamivir resistance in H5N1 influenza A viruses harboring the framework His274Tyr mutation (Le et al., 2005; de Jong et al., 2005) warrant particular attention and careful monitoring for the spreading of resistant variants.

Do the variants isolated from untreated patients demonstrate person-to-person transmissibility in a community or the spontaneous emergence of mutants with reduced drug sensitivity? The global NA Inhibitor Susceptibility Network (NISN) did not identify influenza viruses with resistance to NA inhibitors before these drugs were introduced into clinical use (McKimm-Breshkin et al., 2003; Muscana, 2005), supporting the first possibility. However, in the first 3 years (1999-2002) following the introduction of NA inhibitors to the market, NISN detected a small number (eight out of 2287 isolates, 0.33%) of influenza viruses, isolated from untreated patients, with decreased susceptibility to NA inhibitors (Monto et al., 2006). Of those, two possessed NA mutations previously identified in NA-inhibitor resistant viruses. Moreover, in the 2003-2004 influenza season, NISN identified three H3N2 viruses in 1180 samples collected in Japan that contained NA mutations conferring resistance to NA inhibitors, although it was not possible to determine with certainty whether these patients had been exposed to NA inhibitors or NA inhibitor-treated individuals (WTTO, 2005). The present findings are consistent with these surveillance data, which imply a possible transmission of NA inhibitor-resistant viruses from person to person.

When healthy children were given oseltamivir at 2 mg/kg, the mean peak plasma concentration of oseltamivir carboxylate, the active metabolite of the drug, was 630 nmol/L among children aged 3-5 years and 426 nmol/L among children aged 1-2 years (Oo et al., 2003). This indicates that the $IC_{50}$ values for influenza B viruses tested against oseltamivir in the present study were close to the plasma drug concentration, suggesting that this drug may not be as effective against influenza B virus as against influenza A virus. By contrast, the concentration of zanamivir in the human respiratory tract is estimated to be more than 10,000 mol/L when healthy adults inhale 10 mg zanamivir (Cass et al., 1999), well above the influenza B virus $IC_{50}$ values.

In Japan, prescriptions for oseltamivir were estimated to be 90 times more common than those for zanamivir during the 2004-2005 influenza season (information from the Ministry of Health, Labor and Welfare of Japan). It is therefore possible that the mutants with reduced drug sensitivity found in communities in this study had been generated by widespread use of oseltamivir. Continued surveillance for the emergence or spread of NA inhibitor-resistant influenza viruses is critically important.

Finally, the clinical course of influenza B virus infection in this study did not appear to be affected by the sensitivity of the virus to NA inhibitors, although larger numbers of cases will need to be studied to confirm this impression. Nonetheless, the symptoms of patients from whom viruses with varying sensitivities to NA inhibitors were isolated were similar, indicating that these mutant viruses, at least those carrying the framework mutation, do not lose virulence even though they have evolved to a status that is less sensitive to the drug. Further evaluation of the biologic properties of NA inhibitor-resistant influenza viruses is needed to fully assess their pathogenicity in humans.

EXAMPLE 2

Methods

Viruses and Cells

A wild-type influenza B virus (B/Yokohama/UT38/2005) was passaged in two cell types: Madin-Darby canine kidney (MDCK) cells and MDCK cells overexpressing the β-galactoside α2,6-sialyltransferase I (ST6Gal I) gene. The latter cells were manipulated to express a larger amount of sialyloligosaccharides containing terminal N-acetyl sialic acid linked to galactose by an alpha 2,6-linkage (NeuAcα2,6Gal). These modified cells mimic the receptor environment of human airway cells and better support the growth of clinical isolates of human influenza viruses compared to non-manipulated MDCK cells (Hatakeyama et al., 2005).

Passage of Influenza B Virus in Cells

Confluent monolayers of MDCK cells or ST6Gal I-expressing MDCK cells, grown in 24-well tissue culture plates, were inoculated with 100 μL of virus serially diluted from $10^{-3}$ to $10^{-8}$. After one hour at 37° C., the inoculum was removed and the cells were overlaid with 1 mL of infection medium containing 0.1% agarose with 1 μmol/L neuraminidase (NA) inhibitor. The NA inhibitors used were oseltamivir carboxylate (GS4071; Roche Products, Basel, Switzerland), the active metabolite of the ethyl ester pro-drug oseltamivir phosphate, and zanamivir (Relenza; GlaxoSmithKline, Brentford, UK). Cells were then cultured at 33° C. for 3-4 days. Following this incubation, the supernatant from a well of the second lowest inoculum concentration to show cytopathic effects was harvested, and passaged sequentially 20 times in each cell line with 1 μmol/L oseltamivir or zanamivir as described above.

Sialidase Sensitivity to NA Inhibitors and Sequence Analyses of the NA and HA Genes Sialidase sensitivities of influenza B viruses to NA inhibitors were assessed using sialidase 2'-(4-methylumbelliferyl)-α-D-N-acetylneuraminic acid (MUNANA; Sigma, St. Louis, Mo., USA) in a fluorescence-based sialidase inhibition assay. Strains that demonstrated reduced susceptibility to the inhibitors had their NA and hemagglutinin (HA) genes sequenced after two rounds of plaque-purification, and the concentration of NA inhibitor required to inhibit 50% of the NA sialidase activity of these viruses ($IC_{50}$) was determined.

Viral RNA was extracted from virus in cell-culture supernatant fluid, reverse transcribed, and the resultant cDNA PCR amplification as described in Example 1. The PCR products were cloned into the pCRBlunt II-TOPO vector (Invitrogen, Carlsbad, Calif., USA), which was then used to transform TOP 10 cells (Invitrogen). Transformed cells were grown on Luria broth agar containing 50 mg/L kanamycin until kanamycin-resistant colonies could be selected and incubated in Luria broth at 37° C. overnight in a shaking incubator. Plasmid DNA was extracted with the MagExtractor-plasmid system (TOYOBO, Osaka, Japan). The sequences of the entire NA and HA genes were determined by cycle sequencing with dye-terminator chemistry (Big Dye; Applied Biosystems, Foster City, Calif., USA) on an Applied Biosystems 3130X1 Auto Sequencer using M13F-20, with NA- or HA-specific primers. Five to eight cDNA clones of the NA and HA genes were analyzed for each sample. For viruses cloned by plaque purification, the DNA products of their NA and HA genes were purified and the purified PCR fragments directly sequenced using NA- or HA-specific primers. Amino acid numbering of NA was based on the N2 NA of influenza A virus (Colman et al., 1995), whereas that for HA was based on influenza B HA.

Results

Figure 5:
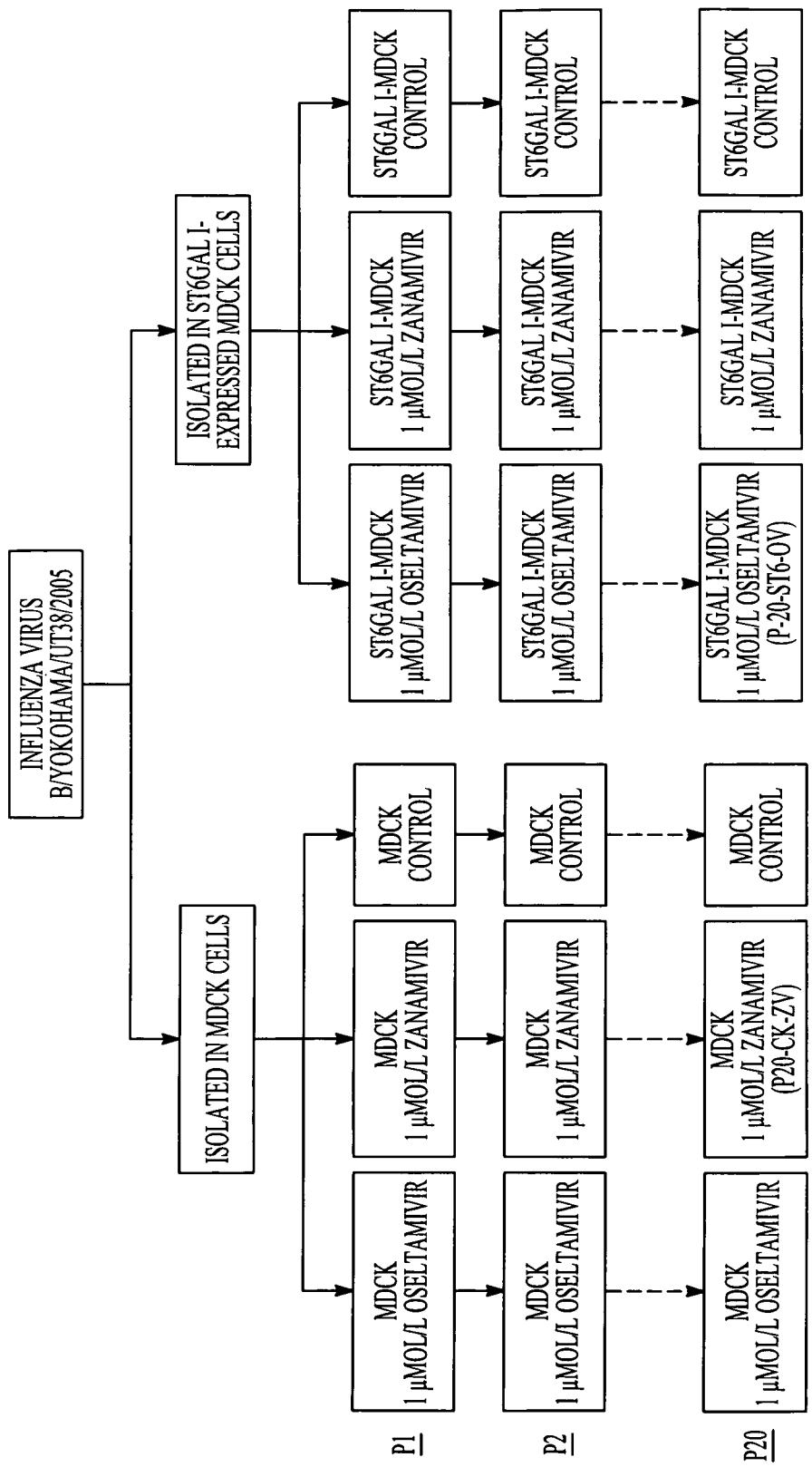
FIG. 5. Passage history of influenza B virus cultured in cells in the presence or absence of NA inhibitors.

The passage history of the virus used in this study is shown in FIG. 5. Following the twentieth passage of virus in the presence of NA inhibitors, the viral $IC_{50}$ values to oseltamivir and zanamivir was determined using a sialidase inhibition assay. Viruses obtained from a twentieth passage in MDCK cells with 1 μmol/L zanamivir (P20-CK-ZV) and a twentieth passage in ST6Gal I-expressing MDCK cells with 1 μmol/L oseltamivir (P20-ST6-OV) had reduced sensitivity to each NA inhibitor, whereas the remaining viruses (i.e., those passaged in MDCK cells with oseltamivir, in the ST6-Gal I-expressing MDCK cells with zanamivir, and in both cells in the absence of inhibitors) remained sensitive to the drugs even after twenty passages.

To identify the NA or HA mutation responsible for conferring resistance to NA inhibitors, the NA and HA genes from the two viruses that exhibited reduced sensitivity to the drugs were cloned and sequenced. The sequence analysis revealed an Asp198Asn substitution in six of the nine cDNA clones of the NA gene and an Arg426Gly substitution in all seven of the cDNA clones of the HA gene from the virus passaged with zanamivir (P20-CK-ZV). An Ile222Thr substitution was found in five of the eight cDNA clones of the NA gene and an Ile337Thr substitution in five of the seven cDNA clones of the HA gene of the virus passaged with oseltamivir (P20-ST6-OV) (Table 2). Retrospective analyses showed that the NA Asp198Asn substitution began to coexist after 12 passages with zanamivir, and that the NA Ile221Thr substitution emerged after 18 passages with oseltamivir (Table 2).

TABLE 2

Number of mutated cDNA clones found in the variants generated by in vitro selection

| | Mutations | | | Mutations | |
| --- | --- | --- | --- | --- | --- |
| | NA | HA | | NA | HA |
| Virus | Asp198Asn | Arg426Gly | Virus | Ile222Thr | Ile337Thr |
| P10-CK-ZV | 0/5 clone | 0/6 clone | P16-ST6-OV | 0/8 clone | 0/8 clone |
| P12-CK-ZV | 1/8 clone | NA | P17-ST6-OV | 0/8 clone | NA |
| P14-CK-ZV | 2/7 clone | NA | P18-ST6-OV | 5/7 clone | 8/8 clone |
| P15-CK-ZV | 7/7 clone | 0/7 clone | P20-ST6-OV | 5/8 clone | 5/7 clone |
| P16-CK-ZV | 4/5 clone | NA | | | |
| P20-CK-ZV | 6/9 clone | 7/7 clone | | | |

To isolate the mutated strains from the mixed populations, two cycles of plaque purification were performed using viruses obtained from a fifteenth passage in MDCK cells with zanamivir (P15-CK-ZV), P20-CK-ZV and P20-ST6-OV, and then sequenced the plaque-purified clonal viruses. Three viruses were obtained: one possessing the NA Asp198Asn substitution with no HA mutation (PP-P15-CK-ZV), one with the NA Asp198Asn substitution and the HA Arg426Gly substitution (PP-P20-CK-ZV), and one with the NA Ile222Thr substitution and the HA Ile337Thr substitution (PP-P20-ST6-OV) (Table 3). Even after extensive plaque purification, viruses possessing only the NA mutation without the HA Ile337Thr substitution from the P20-ST6-OV virus were not obtained.

The $IC_{50}$ values for oseltamivir and zanamivir for the original virus (B/Yokohama/UT38/2005) were 72.5 nmol/L and 10.3 nmol/L, respectively. The $IC_{50}$ values of PP-P15-CK-ZV (NA Asp198Asn), PP-P20-CK-ZV (NA Asp198Asn and HA Arg426Gly) and PP-P20-ST6-OV (NA Ile222Thr and HA Ile337Thr) were 202.8 nmol/L for oseltamivir, 50.5 nmol/L for zanamivir, 235.4 nmol/L for oseltamivir, 59.4 nmol/L for zanamivir, and 523.3 nmol/L for oseltamivir and 21.6 nmol/L for zanamivir, respectively (Table 3). The NA Asp198Asn mutation, therefore, conferred 2.8-3.6-fold resistance to oseltamivir and 4.9-5.8-fold resistance to zanamivir, and the NA Ile222Thr mutation conferred 7.2-fold resistance to oseltamivir and 2.1-fold resistance to zanamivir (Table 3).

TABLE 3

IC$_{50}$ values of plaque-purified variants with reduced sensitivity to NA inhibitors

| Virus | Mutation in NA | Mutation in HA | IC$_{50}$ value, nmol/L (fold change compared with the wild-type virus) oseltamivir | IC$_{50}$ value, nmol/L (fold change compared with the wild-type virus) zanamivir |
|---|---|---|---|---|
| Wild-type | — | — | 72.5 | 10.3 |
| PP-P15-CK-ZV | Asp198Asn | — | 202.8 (2.8-fold) | 50.5 (4.9-fold) |
| PP-P20-CK-ZV | Asp198Asn | Arg426Gly | 235.4 (3.2-fold) | 59.4 (5.8-fold) |
| PP-P20-ST6-OV | Ile222Thr | Ile337Thr | 523.3 (7.2-fold) | 21.6 (2.1-fold) |

Discussion

After more than 12 passages in the presence of NA inhibitors in vitro, resistant influenza B viruses were generated. These resistant viruses possess the NA mutation, Asp198Asn or Ile222Thr, which are the same mutations found in NA inhibitor-resistant viruses isolated from patients.

REFERENCES

Burmeister et al., *EMBO J.*, 11:49 (1992).
Carr et al., *Antiviral Res.*, 54:79 (2002).
Cass et al., *Clin. Pharmacokinet.*, 36:21 (1999).
Centers for Disease Control and Prevention, *MMWR Recomm. Rep.*, 54:1 (2005).
Colman et al., *J. Virol.*, 67:2972 (1993).
De Clercq, *J. Clin. Virol.*, 30:115 (2004).
de Jong et al., *N. Engl. J. Med.*, 353:2667 (2005).
Gubareva et al., *J. Infect. Dis.*, 178:1257 (1998).
Gubareva et al., *J. Infect. Dis.*, 183:523 (2001).
Gubareva, *Virus Res.*, 103:199 (2004).
Hatakeyama et al., *J. Clin. Microbiol.*, 43:4139 (2005).
Herlocher et al., *Antiviral Res.*, 54:99 (2002).
Herlocher et al., *J. Infect. Dis.*, 190:1627 (2004).
Ives et al., *Antiviral Res.*, 55:307 (2002).
Kiso et al., *Lancet*, 364:759 (2004).
Le et al., *Nature*, 437:1108 (2005).
McKimm-Breschkin et al., *Antimicrob. Agents Chemother.*, 47:2264 (2003).
McKimm-Breschkin, *Antiviral Res.*, 47:1 (2000).
Mishin et al., *Antimicrob. Agents Chemother.*, 49:4515 (2005).
Monto et al., *Antimicrob. Agents Chemother.*, 50:2395 (2006).
Moscona, *N. Engl. J. Med.*, 353:1363 (2005).
Oo et al., *Eur. J. Clin. Pharmacol.*, 59:411 (2003).
Pillay et al., *BMJ.*, 317:660 (1998).
Roche. Factsheet Tamiflu. December 2005. Available at: http://www.roche.com/med_mbtamiflu05e.pdf. Accessed Jul. 1, 2006.
Treanor, In: Mandell G L, Bennett J E, Dolin R, ed. *Principles and practice of infectious diseases*, Philadelphia, Pa., USA: Elsevier/Churchill Livingstone; 6:2060 (2005).
Ward et al., *J. Antimicrob. Chemother.*, 55:i5 (2005).
Whitley et al., *Pediatr. Infect. Dis. J.*, 20:127 (2001).
World Health Organization, *Wkly. Epidemiol. Rec.*, 80:156 (2005).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method to select a neuraminidase (NA) inhibitor for a mammal infected with an influenza B virus, comprising:
   detecting in a sample from the mammal an influenza virus neuraminidase (NA) with a residue other than Ile at position 222, other than Ser at position 250, other than Gly at position 402, or a combination thereof, wherein the numbering for NA residues is that for N2, which residue other than Ile at position 222, Ser at position 250, or Gly at position 402 is associated with reduced sensitivity to peramivir, oseltamivir or zanamivir; and
   administering a NA inhibitor effective to treat the mammal which inhibitor is selected based on the residue at position 222, at position 250, or at position 402.

2. The method of claim 1 wherein the NA further comprises a residue at position 198 other than Asp.

3. The method of claim 2 wherein the residue at position 198 is Asn.

4. The method of claim 1 wherein the residue at position 222 is Thr.

5. The method of claim 1 wherein the residue at position 250 is Gly.

6. The method of claim 1 wherein the residue at position 402 is Ser.

7. The method of claim 1 wherein the sample is a pharyngeal sample.

8. The method of claim 1 wherein the sample is a nasal sample.

9. The method of claim 1 wherein the sample is cultured in vitro prior to detection.

10. The method of claim 9 wherein MDCK cells are employed to culture the sample.

11. A method to select a NA inhibitor for a mammal that has not been treated with a NA inhibitor and is suspected of being infected with an influenza B virus, comprising:
    providing a sample from the mammal;
    detecting in the sample an influenza virus NA with a residue other than Asp at position 198, other than Ile at position 222, other than Ser at position 250, other than Gly at position 402, or a combination thereof, wherein the numbering for NA residues is that for N2, which residue other than Asp at position 198, Ile at position 222, Ser at position 250, or Gly at position 402 is associated with reduced sensitivity to peramivir, oseltamivir or zanamivir; and
    administering a NA inhibitor effective to treat the mammal which inhibitor is selected based on the residue at position 198, at position 222, at position 250, or at position 402.

12. A method to select a NA inhibitor for a mammal infected with an influenza B virus, comprising
    providing a mammalian sample suspected of having influenza virus;
    detecting in the sample an influenza B virus NA with a Thr at position 222, a Gly at position 250, or a Ser at position 402, or a combination thereof, wherein the numbering for NA residues is that for N2; and
    administering a NA inhibitor effective to treat the mammal based on whether the virus has a Thr at position 222, a Gly at position 250, or a Ser at position 402.

13. A method to select a NA inhibitor for a mammal that has not been treated with a NA inhibitor and is suspected of being infected with an influenza B virus, comprising:
    providing a sample from the mammal; and
    detecting in the sample an influenza B virus NA with a Asn at position 198, a Thr at position 222, a Gly at position 250, or a Ser at position 402, or a combination thereof, wherein the numbering for NA residues is that for N2; and
    administering a NA inhibitor effective to treat the mammal based on whether the virus has Asn at position 198, Thr at position 222, Gly at position 250, or Ser at position 402.

14. The method of claim 12 or 13 wherein the sample is a pharyngeal sample.

15. The method of claim 12 or 13 wherein the sample is a nasal sample.

16. The method of claim 12 or 13 wherein the sample is a human sample.

17. A method to treat a human infected with an influenza B virus with reduced sensitivity to a NA inhibitor, comprising:
    providing a human infected with
    an influenza B virus having a NA with a Thr at position 222, a Gly at position 250, or a Ser at position 402, or a combination thereof, wherein the numbering for NA residues is that for N2, wherein an influenza B virus NA with a Thr at position 222, a Gly at position 250, or a Ser at position 402 is indicative of a virus with reduced sensitivity to a NA inhibitor; and
    treating the human with a NA inhibitor that is selected based on whether the virus has Thr at position 222, Gly at position 250, or Ser at position 402.

* * * * *

SEQUENCE LISTING

```
<160> NUMBER OF SEQ ID NOS: 21

<210> SEQ ID NO 1
<211> LENGTH: 15
<212> TYPE: DNA
<213> ORGANISM: Artificial Sequence
<220> FEATURE:
<223> OTHER INFORMATION: A synthetic oligonucleotide

<400> SEQUENCE: 1
agcagaagca gagca                                                        15

<210> SEQ ID NO 2
<211> LENGTH: 469
<212> TYPE: PRT
<213> ORGANISM: Influenza virus

<400> SEQUENCE: 2

Met Asn Pro Asn Gln Lys Ile Ile Thr Ile Gly Ser Val Ser Leu Thr
 1               5                  10                  15

Ile Ala Thr Val Cys Phe Leu Met Gln Ile Ala Ile Leu Val Thr Thr
            20                  25                  30

Val Thr Leu His Phe Lys Gln His Glu Cys Asp Ser Pro Ala Ser Asn
        35                  40                  45

Gln Val Met Pro Cys Glu Pro Ile Ile Ile Glu Arg Asn Ile Thr Glu
    50                  55                  60
```

```
Ile Val Tyr Leu Asn Asn Thr Thr Ile Glu Lys Glu Ile Cys Pro Lys
 65                  70                  75                  80

Val Val Glu Tyr Arg Asn Trp Ser Lys Pro Gln Cys Gln Ile Thr Gly
             85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Val Lys
            115                 120                 125

Cys Tyr Gln Phe Ala Leu Gly Gln Gly Thr Thr Leu Asp Asn Lys His
130                 135                 140

Ser Asn Asp Thr Val His Asp Arg Ile Pro His Arg Thr Leu Leu Met
145                 150                 155                 160

Asn Glu Leu Gly Val Pro Phe His Leu Gly Thr Arg Gln Val Cys Ile
                165                 170                 175

Ala Trp Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asp
            195                 200                 205

Gly Arg Leu Val Asp Ser Ile Gly Ser Trp Ser Gln Asn Ile Leu Arg
            210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Arg Ile Leu Phe
            245                 250                 255

Ile Glu Glu Gly Lys Ile Val His Ile Ser Pro Leu Ala Gly Ser Ala
            260                 265                 270

Gln His Val Glu Glu Cys Ser Cys Tyr Pro Arg Tyr Pro Gly Val Arg
            275                 280                 285

Cys Ile Cys Arg Asp Asn Trp Lys Gly Ser Asn Arg Pro Val Val Asp
290                 295                 300

Ile Asn Met Glu Asp Tyr Ser Ile Asp Ser Ser Tyr Val Cys Ser Gly
305                 310                 315                 320

Leu Val Gly Asp Thr Pro Arg Asn Asp Asp Arg Ser Ser Asn Ser Asn
            325                 330                 335

Cys Arg Asn Pro Asn Asn Glu Arg Gly Thr Gln Gly Val Lys Gly Trp
            340                 345                 350

Ala Phe Asp Asn Gly Asn Asp Leu Trp Met Gly Arg Thr Ile Ser Lys
            355                 360                 365

Asp Leu Arg Ser Gly Tyr Glu Thr Phe Lys Val Ile Gly Gly Trp Ser
            370                 375                 380

Thr Pro Asn Ser Lys Ser Gln Ile Asn Arg Gln Val Ile Val Asp Ser
385                 390                 395                 400

Asp Asn Arg Ser Gly Tyr Ser Gly Ile Phe Ser Val Glu Gly Lys Ser
            405                 410                 415

Cys Ile Asn Arg Cys Phe Tyr Val Glu Leu Ile Arg Gly Arg Lys Gln
            420                 425                 430

Glu Thr Arg Val Trp Trp Thr Ser Asn Ser Ile Val Val Phe Cys Gly
            435                 440                 445

Thr Ser Gly Thr Tyr Gly Thr Gly Ser Trp Pro Asp Gly Ala Asn Ile
            450                 455                 460

Asn Phe Met Pro Ile
465
```

```
<210> SEQ ID NO 3
<211> LENGTH: 454
<212> TYPE: PRT
<213> ORGANISM: Influenza virus

<400> SEQUENCE: 3

Met Asn Pro Asn Gln Lys Ile Ile Thr Ile Gly Ser Ile Cys Leu Val
1               5                   10                  15

Val Gly Leu Ile Ser Leu Ile Leu Gln Ile Gly Asn Ile Ile Ser Ile
            20                  25                  30

Trp Ile Ser His Ser Ile Gln Thr Gly Ser Gln Asn His Thr Gly Ile
        35                  40                  45

Cys Asn Gln Asn Ile Ile Thr Tyr Lys Asn Ser Thr Trp Val Lys Asp
    50                  55                  60

Thr Thr Ser Val Ile Leu Thr Gly Asn Ser Ser Leu Cys Pro Ile Arg
65                  70                  75                  80

Gly Trp Ala Ile Tyr Ser Lys Asp Asn Ser Ile Arg Ile Gly Ser Lys
                85                  90                  95

Gly Asp Val Phe Val Ile Arg Glu Pro Phe Ile Ser Cys Ser His Leu
            100                 105                 110

Glu Cys Arg Thr Phe Phe Leu Thr Gln Gly Ala Leu Leu Asn Asp Arg
        115                 120                 125

His Ser Asn Gly Thr Val Lys Asp Arg Ser Pro Tyr Arg Ala Leu Met
    130                 135                 140

Ser Cys Pro Val Gly Glu Ala Pro Ser Pro Tyr Asn Ser Arg Phe Glu
145                 150                 155                 160

Ser Val Ala Trp Ser Ala Ser Ala Cys His Asp Gly Met Gly Trp Leu
                165                 170                 175

Thr Ile Gly Ile Ser Gly Pro Asp Asn Gly Ala Val Ala Val Leu Lys
            180                 185                 190

Tyr Asn Gly Ile Ile Thr Glu Thr Ile Lys Ser Trp Arg Lys Lys Ile
        195                 200                 205

Leu Arg Thr Gln Glu Ser Glu Cys Ala Cys Val Asn Gly Ser Cys Phe
    210                 215                 220

Thr Ile Met Thr Asp Gly Pro Ser Asp Gly Leu Ala Ser Tyr Lys Ile
225                 230                 235                 240

Phe Lys Ile Glu Lys Gly Lys Val Thr Lys Ser Ile Glu Leu Asn Ala
                245                 250                 255

Pro Asn Ser His Tyr Glu Glu Cys Ser Cys Tyr Pro Asp Thr Gly Lys
            260                 265                 270

Val Met Cys Val Cys Arg Asp Asn Trp His Gly Ser Asn Arg Pro Trp
        275                 280                 285

Val Ser Phe Asp Gln Asn Leu Asp Tyr Gln Ile Gly Tyr Ile Cys Ser
    290                 295                 300

Gly Val Phe Gly Asp Asn Pro Arg Pro Lys Asp Gly Thr Gly Ser Cys
305                 310                 315                 320

Gly Pro Val Tyr Val Asp Gly Ala Asn Gly Val Lys Gly Phe Ser Tyr
                325                 330                 335

Arg Tyr Gly Asn Gly Val Trp Ile Gly Arg Thr Lys Ser His Ser Ser
            340                 345                 350

Arg His Gly Phe Glu Met Ile Trp Asp Pro Asn Gly Trp Thr Glu Thr
        355                 360                 365

Asp Ser Lys Phe Ser Val Arg Gln Asp Val Val Ala Met Thr Asp Trp
    370                 375                 380

Ser Gly Tyr Ser Gly Ser Phe Val Gln His Pro Glu Leu Thr Gly Leu
```

```
                385                 390                 395                 400

Asp Cys Ile Arg Pro Cys Phe Trp Val Glu Leu Ile Arg Gly Arg Pro
                405                 410                 415

Lys Glu Lys Thr Ile Trp Thr Ser Ala Ser Ser Ile Ser Phe Cys Gly
                420                 425                 430

Val Asn Ser Asp Thr Val Asp Trp Ser Trp Pro Asp Gly Ala Glu Leu
                435                 440                 445

Pro Phe Thr Ile Asp Lys
                450

<210> SEQ ID NO 4
<211> LENGTH: 468
<212> TYPE: PRT
<213> ORGANISM: Influenza virus

<400> SEQUENCE: 4

Met Asn Pro Asn Gln Lys Ile Ile Thr Ile Gly Ser Ala Ser Leu Gly
  1               5                  10                  15

Leu Val Ile Phe Asn Ile Leu Leu His Val Ala Ser Ile Thr Leu Gly
             20                  25                  30

Ile Ile Ser Val Thr Lys Asp Asn Lys Val His Ile Cys Asn Thr Thr
         35                  40                  45

Glu Val Tyr Asn Glu Thr Val Arg Val Glu Thr Val Ile Pro Val
     50                  55                  60

Asn Asn Thr Ile Tyr Leu Asn His Glu Pro Glu Phe Leu Asn Asn Thr
 65                  70                  75                  80

Glu Pro Leu Cys Asp Val Ser Gly Phe Ala Ile Val Ser Lys Asp Asn
                 85                  90                  95

Gly Ile Arg Ile Gly Ser Arg Gly His Ile Phe Val Ile Arg Glu Pro
            100                 105                 110

Phe Val Ser Cys Gly Pro Ser Glu Cys Arg Thr Phe Phe Leu Thr Gln
        115                 120                 125

Gly Ala Leu Leu Asn Asp Lys His Ser Asn Asn Thr Val Lys Asp Arg
    130                 135                 140

Ser Pro Tyr Arg Ala Leu Met Ser Val Pro Leu Gly Ser Ser Pro Asn
145                 150                 155                 160

Ala Tyr Gln Ala Lys Phe Glu Ser Val Gly Trp Ser Ala Thr Ala Cys
                165                 170                 175

His Asp Gly Lys Lys Trp Met Ala Ile Gly Val Ser Gly Ala Asp Asp
            180                 185                 190

Asp Ala Tyr Ala Val Ile His Tyr Gly Gly Val Pro Thr Asp Val Ile
        195                 200                 205

Arg Ser Trp Arg Lys Gln Ile Leu Arg Thr Gln Glu Ser Ser Cys Val
    210                 215                 220

Cys Ile Lys Gly Glu Cys Tyr Trp Val Met Thr Asp Gly Pro Ala Asn
225                 230                 235                 240

Asn Gln Ala Ser Tyr Lys Ile Phe Lys Ser Gln Lys Gly Met Val Val
                245                 250                 255

Asp Glu Lys Glu Ile Ser Phe Gln Gly Gly His Ile Glu Glu Cys Ser
            260                 265                 270

Cys Tyr Pro Asn Met Gly Lys Val Glu Cys Val Cys Arg Asp Asn Trp
        275                 280                 285

Asn Gly Met Asn Arg Pro Ile Leu Ile Phe Asp Glu Lys Leu Glu Tyr
    290                 295                 300

Glu Val Gly Tyr Leu Cys Ala Gly Ile Pro Thr Asp Thr Pro Arg Val
```

```
              305                 310                 315                 320
Gln Asp Ser Ser Phe Thr Gly Ser Cys Thr Asn Ala Val Gly Arg Ser
                325                 330                 335

Gly Thr Asn Asn Tyr Gly Val Lys Gly Phe Gly Phe Arg Gln Gly Asn
                340                 345                 350

Ser Val Trp Ala Gly Arg Thr Ile Ser Val Ser Ser Arg Ser Gly Phe
                355                 360                 365

Glu Val Leu Leu Ile Glu Asp Gly Trp Ile Arg Pro Ser Lys Thr Ile
            370                 375                 380

Ser Lys Lys Val Glu Val Leu Asn Asn Lys Asn Trp Ser Gly Tyr Ser
385                 390                 395                 400

Gly Ala Phe Thr Ile Pro Thr Ala Met Thr Ser Lys Asn Cys Ile Val
                405                 410                 415

Pro Cys Phe Trp Leu Glu Met Ile Arg Gly Lys Pro Glu Glu Arg Thr
                420                 425                 430

Ser Ile Trp Thr Ser Ser Ser Thr Val Phe Cys Gly Val Ser Ser
                435                 440                 445

Glu Val Pro Gly Trp Ser Trp Asp Asp Gly Ala Ile Leu Pro Phe Asp
            450                 455                 460

Ile Asp Lys Met
465

<210> SEQ ID NO 5
<211> LENGTH: 469
<212> TYPE: PRT
<213> ORGANISM: Influenza virus

<400> SEQUENCE: 5

Met Asn Pro Asn Gln Lys Leu Phe Ala Ser Ser Gly Ile Ala Ile Val
  1               5                  10                  15

Leu Gly Ile Ile Asn Leu Leu Ile Gly Ile Ser Asn Met Ser Leu Asn
                 20                  25                  30

Ile Ser Leu Tyr Ser Lys Gly Glu Ser His Lys Asn Asn Asn Leu Thr
             35                  40                  45

Cys Thr Asn Ile Asn Gln Asn Asp Thr Thr Met Val Asn Thr Tyr Ile
         50                  55                  60

Asn Asn Ala Thr Ile Ile Asp Lys Ser Thr Lys Ile Glu Asn Pro Gly
 65                  70                  75                  80

Tyr Leu Leu Leu Asn Lys Ser Leu Cys Asn Val Glu Gly Trp Val Val
                 85                  90                  95

Ile Ala Lys Asp Asn Ala Ile Arg Phe Gly Glu Ser Glu Gln Ile Ile
                100                 105                 110

Val Thr Arg Glu Pro Tyr Val Ser Cys Asp Pro Leu Ser Cys Lys Met
            115                 120                 125

Tyr Ala Leu His Gln Gly Thr Thr Ile Arg Asn Lys His Ser Asn Ser
130                 135                 140

Thr Thr His Asp Arg Thr Ala Phe Arg Gly Leu Ile Ser Thr Pro Leu
145                 150                 155                 160

Gly Ser Pro Pro Thr Val Ser Asn Ser Glu Phe Ile Cys Val Gly Trp
                165                 170                 175

Ser Ser Thr Ser Cys His Asp Gly Val Asn Arg Met Thr Ile Cys Val
            180                 185                 190

Gln Gly Asp Asn Glu Asn Ala Thr Ala Thr Val Tyr Tyr Asn Lys Arg
        195                 200                 205

Leu Thr Thr Thr Ile Lys Thr Trp Ala Lys Asn Ile Leu Arg Thr Gln
```

```
            210                 215                 220
Glu Ser Glu Cys Val Cys His Asn Ser Thr Cys Val Val Met Thr
225                 230                 235                 240

Asp Gly Pro Ala Asn Asn Gln Ala Phe Thr Lys Val Ile Tyr Phe His
                245                 250                 255

Lys Gly Met Ile Ile Lys Glu Glu Ser Leu Lys Gly Ser Ala Lys His
                260                 265                 270

Ile Glu Glu Cys Ser Cys Tyr Gly His Asn Gln Arg Val Thr Cys Val
                275                 280                 285

Cys Arg Asp Asn Trp Gln Gly Ala Asn Arg Pro Ile Ile Glu Ile Asp
290                 295                 300

Met Asn Lys Leu Glu His Thr Ser Arg Tyr Ile Cys Thr Gly Val Leu
305                 310                 315                 320

Thr Asp Thr Ser Arg Pro Lys Asp Lys Thr Ile Gly Glu Cys Phe Asn
                325                 330                 335

Pro Ile Thr Gly Ser Pro Gly Ala Pro Gly Ile Lys Gly Phe Gly Phe
                340                 345                 350

Leu Asn Glu Asp Asn Thr Trp Leu Gly Arg Thr Ile Ser Pro Arg Leu
                355                 360                 365

Arg Ser Gly Phe Glu Met Leu Lys Ile Pro Asn Ala Gly Thr Asp Pro
370                 375                 380

Glu Ser Lys Ile Lys Glu Arg Gln Glu Ile Val Ser Asn Asp Asn Trp
385                 390                 395                 400

Ser Gly Tyr Ser Gly Ser Phe Ile Asp Tyr Trp Asn Asp Asn Ser Glu
                405                 410                 415

Cys Tyr Asn Pro Cys Phe Tyr Val Glu Leu Ile Arg Gly Arg Pro Glu
                420                 425                 430

Glu Ala Lys Tyr Val Glu Trp Thr Ser Asn Ser Leu Ile Ala Leu Cys
                435                 440                 445

Gly Ser Pro Ile Ser Val Gly Ser Gly Ser Phe Pro Asp Gly Ala Gln
                450                 455                 460

Ile Lys Tyr Phe Ser
465

<210> SEQ ID NO 6
<211> LENGTH: 470
<212> TYPE: PRT
<213> ORGANISM: Influenza virus

<400> SEQUENCE: 6

Met Asn Pro Asn Gln Lys Ile Ile Ala Ile Gly Ser Ala Ser Leu Gly
1               5                   10                  15

Ile Leu Ile Leu Asn Val Ile Leu His Val Val Ser Ile Val Val Thr
                20                  25                  30

Val Leu Val Leu Asn Asn Asn Gly Thr Gly Leu Asn Cys Asn Gly Thr
                35                  40                  45

Ile Ile Arg Glu Tyr Asn Glu Thr Val Arg Val Glu Arg Ile Thr Gln
            50                  55                  60

Trp Tyr Asn Thr Asn Thr Ile Glu Tyr Ile Glu Arg Pro Ser Asn Glu
65              70                  75                  80

Tyr Tyr Met Asn Asn Thr Glu Pro Leu Cys Glu Ala Gln Gly Phe Ala
                85                  90                  95

Pro Phe Ser Lys Asp Asn Gly Ile Arg Ile Gly Ser Arg Gly His Val
                100                 105                 110

Phe Val Ile Arg Glu Pro Phe Val Ser Cys Ser Pro Leu Glu Cys Arg
```

```
                115                 120                 125
Thr Phe Phe Leu Thr Gln Gly Ser Leu Leu Asn Asp Lys His Ser Asn
130                 135                 140

Gly Thr Val Lys Asp Arg Ser Pro Tyr Arg Thr Leu Met Ser Val Lys
145                 150                 155                 160

Val Gly Gln Ser Pro Asn Val Tyr Gln Ala Arg Phe Glu Ser Val Ala
                165                 170                 175

Trp Ser Ala Thr Ala Cys His Asp Gly Lys Lys Trp Met Thr Val Gly
            180                 185                 190

Val Thr Gly Pro Asp Asn Gln Ala Val Ala Val Val Asn Tyr Gly Gly
        195                 200                 205

Val Pro Val Asp Ile Ile Asn Ser Trp Gly Arg Asp Ile Leu Arg Thr
    210                 215                 220

Gln Glu Ser Ser Cys Thr Cys Ile Lys Gly Asp Cys Tyr Trp Val Met
225                 230                 235                 240

Thr Asp Gly Pro Ala Asn Arg Gln Ala Lys Tyr Arg Ile Phe Lys Ala
                245                 250                 255

Lys Asp Gly Arg Ile Ile Gly Gln Thr Asp Ile Ser Phe Asn Gly Gly
            260                 265                 270

His Ile Glu Glu Cys Ser Cys Tyr Pro Asn Glu Gly Lys Val Glu Cys
        275                 280                 285

Val Cys Arg Asp Asn Trp Thr Gly Thr Asn Arg Pro Ile Leu Val Ile
    290                 295                 300

Ser Pro Asp Leu Ser Tyr Thr Val Gly Tyr Leu Cys Ala Gly Ile Pro
305                 310                 315                 320

Thr Asp Thr Pro Arg Gly Glu Asp Ser Gln Phe Thr Gly Ser Cys Thr
                325                 330                 335

Ser Pro Leu Gly Asn Lys Gly Tyr Gly Val Lys Gly Phe Gly Phe Arg
            340                 345                 350

Gln Gly Asn Asp Val Trp Ala Gly Arg Thr Ile Ser Arg Thr Ser Arg
        355                 360                 365

Ser Gly Phe Glu Ile Ile Lys Ile Arg Asn Gly Trp Thr Gln Asn Ser
    370                 375                 380

Lys Asp Gln Ile Arg Lys Gln Val Ile Ile Asp Asn Leu Asn Trp Ser
385                 390                 395                 400

Gly Tyr Ser Gly Ser Phe Thr Leu Pro Val Glu Leu Thr Lys Lys Gly
                405                 410                 415

Cys Leu Val Pro Cys Phe Trp Val Glu Met Ile Arg Gly Lys Pro Glu
            420                 425                 430

Asp Thr Thr Ile Trp Thr Ser Ser Ser Ile Val Met Cys Gly Val
        435                 440                 445

Asp His Lys Ile Ala Ser Trp Ser Trp His Asp Gly Ala Ile Leu Pro
    450                 455                 460

Phe Asp Ile Asp Lys Ile
465                 470

<210> SEQ ID NO 7
<211> LENGTH: 470
<212> TYPE: PRT
<213> ORGANISM: Influenza virus

<400> SEQUENCE: 7

Met Asn Pro Asn Gln Lys Ile Leu Cys Thr Ser Ala Thr Ala Leu Val
1               5                   10                  15

Ile Gly Thr Ile Ala Val Leu Ile Gly Ile Thr Asn Leu Gly Leu Asn
```

```
                     20                  25                  30
Ile Gly Leu His Leu Lys Pro Ser Cys Asn Cys Ser His Ser Gln Pro
             35                  40                  45

Glu Ala Thr Asn Ala Ser Gln Thr Ile Ile Asn Asn Tyr Tyr Asn Asp
         50                  55                  60

Thr Asn Ile Thr Gln Ile Ser Asn Thr Asn Ile Gln Val Glu Glu Arg
65                  70                  75                  80

Ala Ile Arg Asp Phe Asn Asn Leu Thr Lys Gly Leu Cys Thr Ile Asn
                 85                  90                  95

Ser Trp His Ile Tyr Gly Lys Asp Asn Ala Val Arg Ile Gly Glu Asp
             100                 105                 110

Ser Asp Val Leu Val Thr Arg Glu Pro Tyr Val Ser Cys Asp Pro Asp
         115                 120                 125

Glu Cys Arg Phe Tyr Ala Leu Ser Gln Gly Thr Thr Ile Arg Gly Lys
     130                 135                 140

His Ser Asn Gly Thr Ile His Asp Arg Ser Gln Tyr Arg Ala Leu Ile
145                 150                 155                 160

Ser Trp Pro Leu Ser Ser Pro Pro Thr Val Tyr Asn Ser Arg Val Glu
                 165                 170                 175

Cys Ile Gly Trp Ser Ser Thr Ser Cys His Asp Gly Lys Thr Arg Met
             180                 185                 190

Ser Ile Cys Ile Ser Gly Pro Asn Asn Asn Ala Ser Ala Val Ile Trp
         195                 200                 205

Tyr Asn Arg Arg Pro Val Thr Glu Ile Asn Thr Trp Ala Arg Asn Ile
     210                 215                 220

Leu Arg Thr Gln Glu Ser Glu Cys Val Cys His Asn Gly Val Cys Pro
225                 230                 235                 240

Val Val Phe Thr Asp Gly Ser Ala Thr Gly Pro Ala Glu Thr Arg Ile
                 245                 250                 255

Tyr Tyr Phe Lys Glu Gly Lys Ile Leu Lys Trp Glu Pro Leu Ala Gly
             260                 265                 270

Thr Ala Lys His Ile Glu Glu Cys Ser Cys Tyr Gly Glu Arg Ala Glu
         275                 280                 285

Ile Thr Cys Thr Cys Arg Asp Asn Trp Gln Gly Ser Asn Arg Pro Val
     290                 295                 300

Ile Arg Ile Asp Pro Val Ala Met Thr His Thr Ser Gln Tyr Ile Cys
305                 310                 315                 320

Ser Pro Val Leu Thr Asp Asn Pro Arg Pro Asn Asp Pro Thr Val Gly
                 325                 330                 335

Lys Cys Asn Asp Pro Tyr Pro Gly Asn Asn Asn Asn Gly Val Lys Gly
             340                 345                 350

Phe Ser Tyr Leu Asp Gly Val Asn Thr Trp Leu Gly Arg Thr Ile Ser
         355                 360                 365

Ile Ala Ser Arg Ser Gly Tyr Glu Met Leu Lys Val Pro Asn Ala Leu
     370                 375                 380

Thr Asp Asp Lys Ser Lys Pro Thr Gln Gly Gln Thr Ile Val Leu Asn
385                 390                 395                 400

Thr Asp Trp Ser Gly Tyr Ser Gly Ser Phe Met Asp Tyr Trp Ala Glu
                 405                 410                 415

Gly Glu Cys Tyr Arg Ala Cys Phe Tyr Val Glu Leu Ile Arg Gly Arg
             420                 425                 430

Pro Lys Glu Asp Lys Val Trp Trp Thr Ser Asn Ser Ile Val Ser Met
         435                 440                 445
```

Cys Ser Ser Thr Glu Phe Leu Gly Gln Trp Asp Trp Pro Asp Gly Ala
450                 455                 460

Lys Ile Glu Tyr Phe Leu
465                 470

<210> SEQ ID NO 8
<211> LENGTH: 465
<212> TYPE: PRT
<213> ORGANISM: Influenza virus

<400> SEQUENCE: 8

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
                20                  25                  30

Tyr Ser Asp Ile Leu Leu Lys Phe Ser Pro Lys Ile Thr Ala Pro Thr
            35                  40                  45

Met Thr Leu Asp Cys Thr Asn Ala Ser Asn Val Gln Ala Val Asn Arg
50                  55                  60

Ser Ala Thr Lys Glu Met Thr Phe Leu Leu Pro Glu Pro Glu Trp Thr
65                  70                  75                  80

Tyr Pro Arg Leu Ser Cys Gln Gly Ser Thr Phe Gln Lys Ala Leu Leu
                85                  90                  95

Ile Ser Pro His Arg Phe Gly Glu Ala Arg Gly Asn Ser Ala Pro Leu
            100                 105                 110

Ile Ile Arg Glu Pro Phe Ile Ala Cys Gly Pro Lys Glu Cys Lys His
            115                 120                 125

Phe Ala Leu Thr His Tyr Ala Ala Gln Pro Gly Gly Tyr Tyr Asn Gly
130                 135                 140

Thr Arg Glu Asp Arg Asn Lys Leu Arg His Leu Ile Ser Val Lys Leu
145                 150                 155                 160

Gly Lys Ile Pro Thr Val Glu Asn Ser Ile Phe His Met Ala Ala Trp
                165                 170                 175

Ser Gly Ser Ala Cys His Asp Gly Arg Glu Trp Thr Tyr Ile Gly Val
            180                 185                 190

Asp Gly Pro Asp Ser Asn Ala Leu Ile Lys Ile Lys Tyr Gly Glu Ala
            195                 200                 205

Tyr Thr Asp Thr Tyr His Ser Tyr Ala Asn Asn Ile Leu Arg Thr Gln
210                 215                 220

Glu Ser Ala Cys Asn Cys Ile Gly Gly Asp Cys Tyr Leu Met Ile Thr
225                 230                 235                 240

Asp Gly Ser Ala Ser Gly Ile Ser Lys Cys Arg Phe Leu Lys Ile Arg
                245                 250                 255

Glu Gly Arg Ile Ile Lys Glu Ile Phe Pro Thr Gly Arg Val Glu His
            260                 265                 270

Thr Glu Glu Cys Thr Cys Gly Phe Ala Ser Asn Lys Thr Ile Glu Cys
            275                 280                 285

Ala Cys Arg Asp Asn Asn Tyr Thr Ala Lys Arg Pro Phe Val Lys Leu
290                 295                 300

Asn Val Glu Thr Asp Thr Ala Glu Ile Arg Leu Met Cys Thr Glu Thr
305                 310                 315                 320

Tyr Leu Asp Thr Pro Arg Pro Asp Gly Ser Ile Thr Gly Pro Cys
                325                 330                 335

Glu Ser Asn Gly Asp Lys Gly Arg Gly Gly Ile Lys Gly Gly Phe Val
            340                 345                 350

-continued

```
His Gln Arg Met Ala Ser Lys Ile Gly Arg Trp Tyr Ser Arg Thr Met
        355                 360                 365
Ser Lys Thr Glu Arg Met Gly Met Glu Leu Tyr Val Lys Tyr Asp Gly
    370                 375                 380
Asp Pro Trp Thr Asp Ser Asp Ala Leu Asp Pro Ser Gly Val Met Val
385                 390                 395                 400
Ser Ile Lys Glu Pro Gly Trp Tyr Ser Phe Gly Phe Glu Ile Lys Asp
                405                 410                 415
Lys Lys Cys Asp Val Pro Cys Ile Gly Ile Glu Met Val His Asp Gly
            420                 425                 430
Gly Lys Lys Thr Trp His Ser Ala Ala Thr Ala Ile Tyr Cys Leu Met
        435                 440                 445
Gly Ser Gly Gln Leu Leu Trp Asp Thr Val Thr Gly Val Asp Met Ala
    450                 455                 460
Leu
465
```

<210> SEQ ID NO 9
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 9
tattcgtctc agggagcaga agcagagca                                    29

<210> SEQ ID NO 10
<211> LENGTH: 43
<212> TYPE: DNA
<213> ORGANISM: Artificial Sequence
<220> FEATURE:
<223> OTHER INFORMATION: A synthetic oligonucleotide

<400> SEQUENCE: 10
tattcgtctc agggagcaga agcagagcat cttctcaaaa ctg                    43

<210> SEQ ID NO 11
<211> LENGTH: 43
<212> TYPE: DNA
<213> ORGANISM: Artificial Sequence
<220> FEATURE:
<223> OTHER INFORMATION: A synthetic oligonucleotide

<400> SEQUENCE: 11
atatcgtctc gtattagtag taacaagagc attttttcaga aac                   43

<210> SEQ ID NO 12
<211> LENGTH: 42
<212> TYPE: DNA
<213> ORGANISM: Artificial Sequence
<220> FEATURE:
<223> OTHER INFORMATION: A synthetic oligonucleotide

<400> SEQUENCE: 12
tattcgtctc agggagcaga agcagagcat tttctaatat cc                     42

```
<210> SEQ ID NO 13
<211> LENGTH: 48
<212> TYPE: DNA
<213> ORGANISM: Artificial Sequence
<220> FEATURE:
<223> OTHER INFORMATION: A synthetic oligonucleotide

<400> SEQUENCE: 13
atatcgtctc gtattagtag taacaagagc attttttcaat aacgtttc                48

<210> SEQ ID NO 14
<211> LENGTH: 20
<212> TYPE: DNA
<213> ORGANISM: Influenza virus

<400> SEQUENCE: 14
tgcctcagct tgtttctgtc                                                20

<210> SEQ ID NO 15
<211> LENGTH: 21
<212> TYPE: DNA
<213> ORGANISM: Influenza virus

<400> SEQUENCE: 15
gaaagcactc ctaattagcc c                                              21

<210> SEQ ID NO 16
<211> LENGTH: 20
<212> TYPE: DNA
<213> ORGANISM: Influenza virus

<400> SEQUENCE: 16
gacacaagaa agtgcctgca                                                20

<210> SEQ ID NO 17
<211> LENGTH: 22
<212> TYPE: DNA
<213> ORGANISM: Influenza virus

<400> SEQUENCE: 17
gaatggcatc caagattgga ag                                             22

<210> SEQ ID NO 18
<211> LENGTH: 19
<212> TYPE: DNA
<213> ORGANISM: Influenza virus

<400> SEQUENCE: 18
tgtagggtcc tcctggtgc                                                 19

<210> SEQ ID NO 19
<211> LENGTH: 20
<212> TYPE: DNA
<213> ORGANISM: Influenza virus

<400> SEQUENCE: 19
gctttcctat aatgcacgac                                                20

<210> SEQ ID NO 20
<211> LENGTH: 20
<212> TYPE: DNA
<213> ORGANISM: Influenza virus

<400> SEQUENCE: 20
gaattgttgt tgattacatg                                                20
```

```
<210> SEQ ID NO 21
<211> LENGTH: 20
<212> TYPE: DNA
<213> ORGANISM: Influenza virus

<400> SEQUENCE: 21
gatgagaaag tggatgatct                                              20
```